US007198792B2

(12) United States Patent
Regts et al.

(10) Patent No.: US 7,198,792 B2
(45) Date of Patent: Apr. 3, 2007

(54) GENETIC IMMUNIZATION AGAINST CERVICAL CARCINOMA

(75) Inventors: Djoeke Geesje Regts, Groningen (NL); Marijke Holtrop, Groningen (NL); Jan Christiaan Wilschut, Garnwerd (NL); Catharina Arnoldine H. H. Daemen, Leermens (NL)

(73) Assignee: Rijksuniversiteit Groningen, Groningen (NL)

( * ) Notice: Subject to any disclaimer, the term of this patent is extended or adjusted under 35 U.S.C. 154(b) by 556 days.

(21) Appl. No.: 10/406,818

(22) Filed: Apr. 4, 2003

(65) Prior Publication Data

US 2004/0005711 A1    Jan. 8, 2004

Related U.S. Application Data

(63) Continuation of application No. PCT/NL01/00740, filed on Oct. 8, 2001.

(30) Foreign Application Priority Data

Oct. 6, 2000    (EP)    .................................. 00203472

(51) Int. Cl.
*A61K 39/12*    (2006.01)
(52) U.S. Cl. ................ 424/199.1; 424/204.1; 435/320.1
(58) Field of Classification Search ............. 424/199.1, 424/204.1; 435/69.1, 320.1, 6
See application file for complete search history.

(56) References Cited

U.S. PATENT DOCUMENTS

| 5,789,245 | A | 8/1998 | Dubensky, Jr. et al. |
| 5,814,482 | A | 9/1998 | Dubensky, Jr. et al. |
| 5,843,723 | A | 12/1998 | Dubensky, Jr. et al. |
| 6,015,686 | A | 1/2000 | Dubensky, Jr. et al. |
| 6,015,694 | A | 1/2000 | Dubensky, Jr. et al. |
| 6,342,372 | B1 | 1/2002 | Dubensky, Jr. et al. |
| 6,376,236 | B1 | 4/2002 | Dubensky, Jr. et al. |

FOREIGN PATENT DOCUMENTS

EP    0 711 829 A2    5/1996

| WO | WO 99/28487 A1 | 6/1999 |
| WO | WO 02/29074 A2 | 4/2002 |

OTHER PUBLICATIONS

Strauss et al. Microbiological Reviews, 1994, vol. 58, No. 3, pp. 491-562.*
International Prelmiinary Examination Report, International Application No. PCT/NL01/00740, dated Oct. 18, 2002.
International Search Report, International Application No. PCT/NL01/00740, dated Jul. 12, 2002 (3 pages).
Berglund, Peter, et al., "Immunization with recombinant Semliki Forest virus induces protection against influenza challenge in mice," 17(5) VACCINE 497-507 (Feb. 5, 1999).
Borysiewicz, L.K., et al., "A recombinant vaccinia virus encoding human papillomavirus types 16 and 18, E6 and E7 proteins as immunotherapy for cervical cancer," 347(9014) LANCET 1523-27 (Jun. 1, 1996).
Boursnell, M.E.G., et al., "Construction and characterisation of a recombinant vaccinia virus expressing human papillomavirus proteins for immunotherapy of cervical cancer," 14(16) VACCINE 1485-94 (Nov. 1, 1996).
Daemen, T., et al., "Genetic immunization against cervical carcinoma: induction of cytotoxic T Lymphocyte activity with a recombinant alphavirus vector expressing human papillomavirus type 16 E6 and E7," 7(21) Gene Therapy 1859-66 (Nov. 2000).
Heino, Pirkko, et al., "Human Papillomavirus Type 16 Capsid Proteins Produced from Recombinant Semliki Forest Virus Assemble into Virus-like Particles," 214(2) VIROLOGY 349-59 (Dec. 20, 1995).
Withoff, S., et al., "Development of cytokine-transduced, autologous whole-cell cancer vaccines, using recombinant Semliki Forest virus," 39 Proceedings of the American Association for Cancer Research Annual 533 (Mar. 1998).

* cited by examiner

*Primary Examiner*—Ali R. Salimi
(74) *Attorney, Agent, or Firm*—TraskBritt

(57) ABSTRACT

An alphavirus vector system comprising nucleic acid of a human papilloma virus origin is disclosed. A method of treating or preventing cervical cancer is also disclosed. The method includes administering the alphavirus vector system and/or a cell comprising nucleic acid derived from human papilloma virus (HPV) to a subject. The alphavirus vector system or the cell may be administered as a vaccine.

28 Claims, 19 Drawing Sheets

FIGURE 2
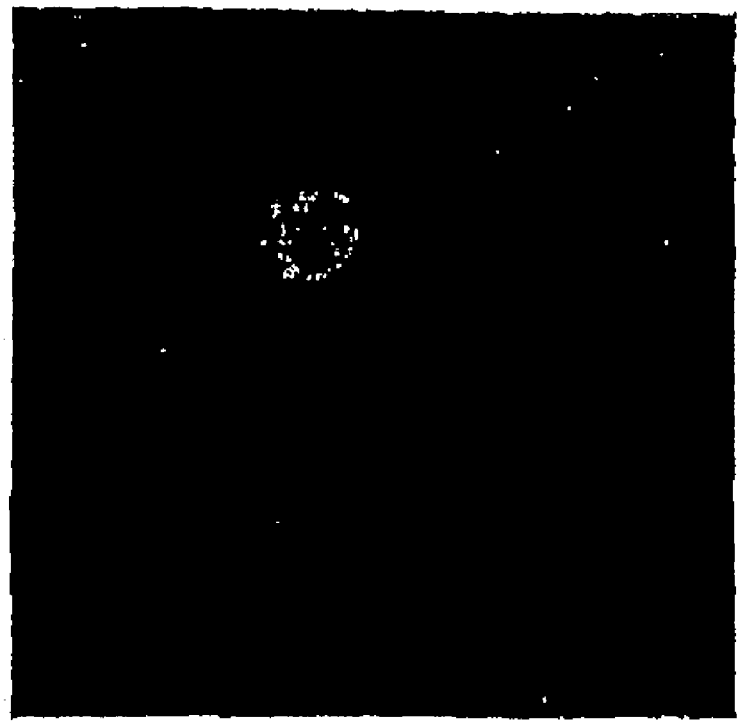
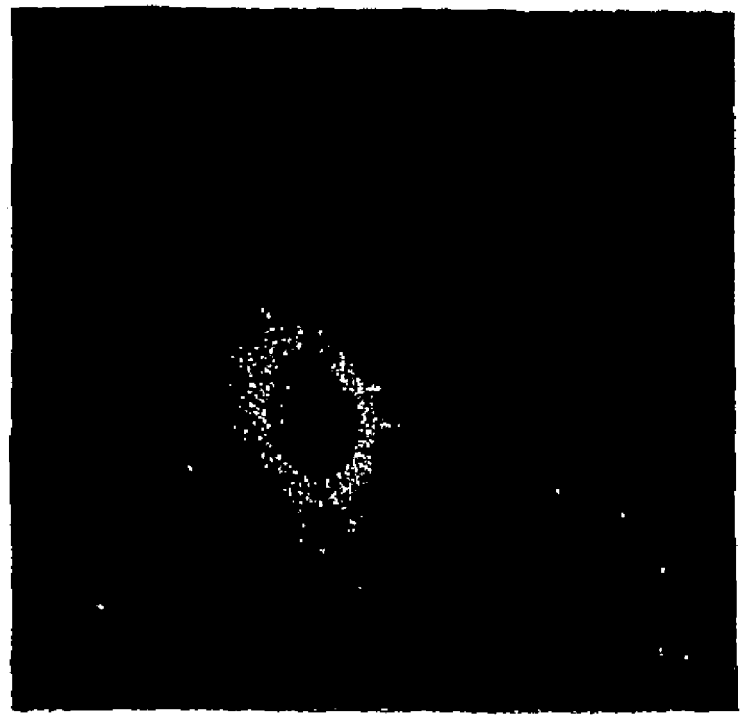

FIGURE 9
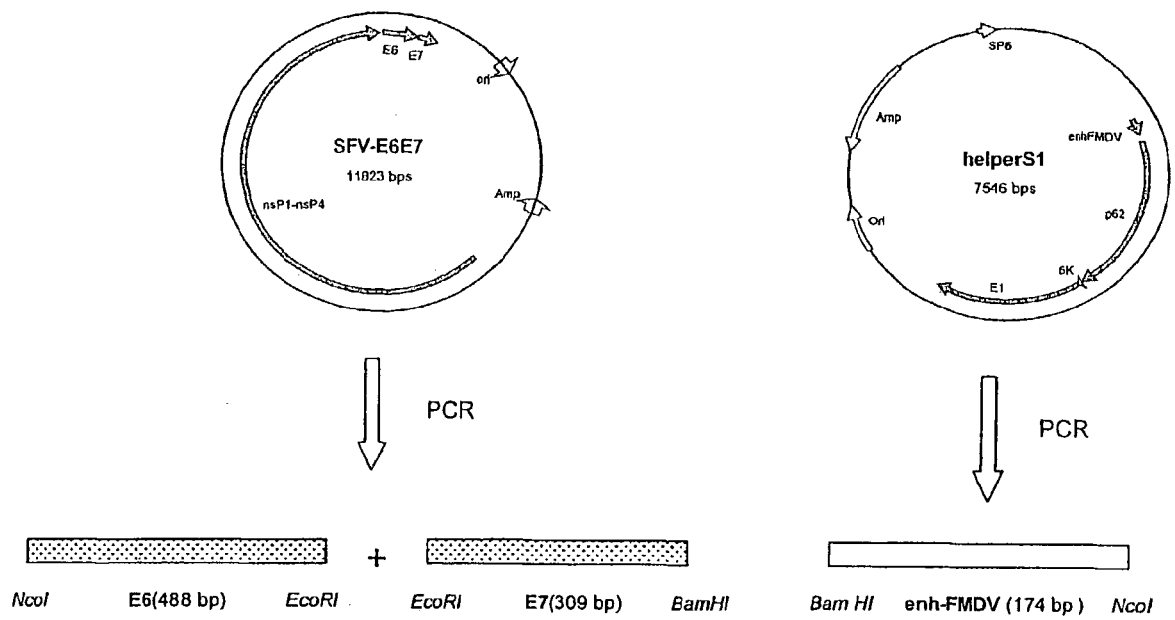
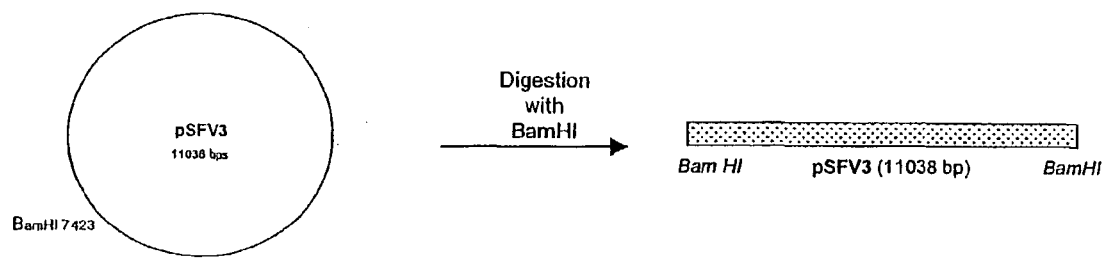
Ligation of the fragments
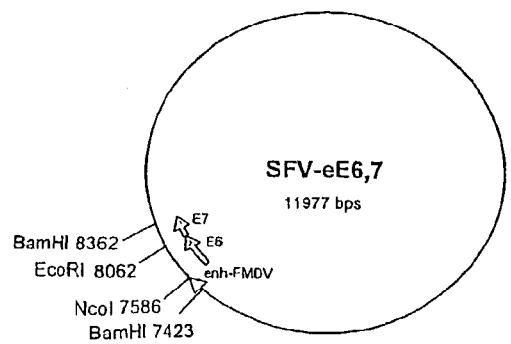

FIGURE 19 enhE6,7 sequence

GATCCAGCACCATGAATTACATCCCTACGCAAACGTTTTACGGCCGCCGGTGGCG
CCCGCGCCCGGCGGCCCGTCCTTGGCCGTTGCAGGCCACTCCGGTGGCTCCCGT
CGTCAATTTTGACCTTCTTAAGCTTGCGGGAGACGTCGAGTCCAACCCTGGGCCC
ATGGACCAAAAGAGAACTGCAATGTTTCAGGACCCACAGGAGCGACCCAGAAAG
TTACCACAGTTATGCACAGAGCTGCAAACAACTATACATGATATAATATTAGAAT
GTGTGTACTGCAAGCAACAGTTACTGCGACGTGAGGTATATGACTTTGCTTTTCG
GGATTTATGCATAGTATATAGAGATGGGAATCCATATGCTGTATGTGATAAATGT
TTAAAGTTTTATTCTAAAATTAGTGAGTATAGACATTATTGTTATAGTTTGTATGG
AACAACATTAGAACAGCAATACAACAAACCGTTGTGTGATTTGTTAATTAGGTGT
ATTAACTGTCAAAAGCCACTGTGTCCTGAAGAAAAGCAAAGACATCTGGACAAAA
AGCAAAGATTCCATAATATAAGGGGTCGGTGGACCGGTCGATGTATGTCTTGTTG
CAGATCATCAAGAACACGTAGAGAAACCCAGCTGGAATTCATGGAGATACACCTA
CATTGCATGAATATATGTTAGATTTGCAACCAGAGACAACTGATCTCTACTGTTAT
GAGCAATTAAATGACAGCTCAGAGGAGGAGGATGAAATAGATGGTCCAGCTGGA
CAAGCAGAACCGGACAGAGCCCATTACAATATTGTAACCTTTTGTTGCAAGTGTG
ACTCTACGCTTCGGTTGTGCGTACAAAGCACACACGTAGACATTCGTACTTTGGA
AGACCTGTTAATGGGCACACTAGGAATTGTGTGCCCATCTGTTCTCAGAAACCA
TAACG    (SEQ ID NO: 4)

SEQUENCE LISTING

<160> NUMBER OF SEQ ID NOS: 5

<210> SEQ ID NO 1
<211> LENGTH: 25
<212> TYPE: DNA
<213> ORGANISM: Artificial sequence
<220> FEATURE:
<223> OTHER INFORMATION: Synthesized sequence, primer E6 forward

<400> SEQUENCE: 1
gacggatcca aagagaactc caatg                                        25

<210> SEQ ID NO 2
<211> LENGTH: 29
<212> TYPE: DNA
<213> ORGANISM: Artificial sequence
<220> FEATURE:
<223> OTHER INFORMATION: Synthesized sequence, primer E7 reverse

<400> SEQUENCE: 2
gagaattcgg atccgccatg gtagattat                                    29

<210> SEQ ID NO 3
<211> LENGTH: 9
<212> TYPE: PRT
<213> ORGANISM: Artificial sequence
<220> FEATURE:
<223> OTHER INFORMATION: Synthesized peptide originating from E7, binds
    to HPV16 H-2Db

<400> SEQUENCE: 3

Arg Ala His Tyr Asn Ile Val Thr Phe
1               5

<210> SEQ ID NO 4
<211> LENGTH: 109
<212> TYPE: DNA
<213> ORGANISM: Artificial sequence
<220> FEATURE:
<223> OTHER INFORMATION: construct enhE6,7

<400> SEQUENCE: 4
gatccagcac catgaattac atccctacgc aaacgtttta cggccgccgg tggcgcccgc     60
gcccggcggc ccgtccttgg ccgttgcagg ccactccggt ggctcccgt                109

<210> SEQ ID NO 5
<211> LENGTH: 10
<212> TYPE: PRT
<213> ORGANISM: Artificial sequence
<220> FEATURE:
<223> OTHER INFORMATION: Adenoviral E1A epitope

<400> SEQUENCE: 5

Ser Gly Pro Ser Asn Thr Pro Pro Glu Ile
1               5                   10

GENETIC IMMUNIZATION AGAINST CERVICAL CARCINOMA

CROSS-REFERENCE TO RELATED APPLICATION

This application is a continuation of PCT International Patent Application No. PCT/NL01/00740, filed on Oct. 8, 2001, designating the United States of America, and published, in English, as PCT International Publication No. WO 02/29074 A2 on Apr. 11, 2002, the contents of the entirety of which are incorporated herein by reference.

TECHNICAL FIELD

The invention relates to the field of cervical cancer caused by human papilloma viruses. Papilloma viruses are small naked DNA tumor viruses (7.9 Kb, double-stranded), which are highly species specific.

BACKGROUND

Over 90 individual human papilloma virus types (HPV) have been described. Genital HPV infection in young, sexually active women is common and most infected individuals either clear the infection, or if lesions do develop, have regression of the lesions. Only a subset of infected individuals develop lesions which progress to a high grade, intraepithelial neoplasia and only a fraction of the intraepithelial neoplasias progress to invasive carcinoma.

Carcinoma of the cervix in a woman develops through a pre-cancerous, intermediate stage to an invasive carcinoma which frequently leads to death. Infection of genital epithelial cells with human papilloma virus (HPV) types 16 and 18 is closely associated with the development of cervical carcinoma. The HPV genome encodes 7 early (E) nonstructural regulatory proteins and two late (L) structural proteins. Integration of the viral DNA in the genome of the host cell, which is considered an essential step in HPV16- or HPV18-induced development of cervical carcinoma, results in a loss of E1- or E2-mediated transcriptional control. As a consequence, the transformed cells over-express the E6 and E7 proteins, thus initiating the malignant transformation process (Pei, Carcinogenesis 1996, 17:1395–1401).

Specific cell-mediated immunity is believed to play an essential role in the control of HPV infections and cervical carcinoma. This assumption is based on observations showing (i) that HPV-induced lesions spontaneously regress in the majority of individuals, and (ii) that immunodeficient patients develop significantly more HPV related proliferative lesions in skin and anogenital tissue than immunocompetent individuals. It has been demonstrated in several animal models that the HPV E6 and E7 proteins, constitutively expressed in HPV transformed cells, can act as targets for CTL-mediated tumor cell killing and stimulation of tumor-specific CTL activity. Induction of an antigen-specific CTL response requires intracellular processing of the target antigen and presentation of antigenic peptides by MHC class I molecules.

In the last few years, a number of peptide/protein-based or genetic immunization strategies have been described for the induction of HPV-specific CTL activity. Drawbacks associated with the peptide-based approach include MHC-polymorphism and the risk of inducing T-cell tolerance rather than T-cell activation. Due to the induction of specific T-cell tolerance, vaccination with a tumor-specific peptide has been shown to result in an enhanced outgrowth of the tumor. Immunization with larger proteins would overcome these problems, but requires efficient antigen delivery systems and/or safe adjuvants for efficient immune priming.

The induction of HPV-specific CTL responses in mice upon immunization with recombinant vaccinia virus that expresses HPV E6 or E7 unexpectedly produced lower titers compared to the parental strain that seriously reduces the effectiveness for inducing HPV-specific CTL responses. Other drawbacks associated with the use of the vaccinia virus-based vector system include immune responses against viral proteins in pre-immune patients or more seriously, integration of recombinant genes into the host cell genome (retrovirus). The risk of integration into the host cell genome is a point of major concern as infected cells can indeed survive and become tumorigenic (immortalized), especially when the recombinant virus encodes oncoproteins such as HPV E6 or E7

SUMMARY OF THE INVENTION

The invention discloses an alphavirus vector system comprising nucleic acid derived from a human papilloma virus (HPV). Alphaviruses include a nucleocapsid with one copy of a single-stranded RNA molecule surrounded by envelope containing spike proteins. Alphavirus RNA has a positive polarity, thus enabling the genomic RNA to initiate an infection when introduced into the cytoplasm of a cell. Further, the RNA is self-replicating since it encodes its own replicase, wherein replication results in high-level expression of the viral proteins in host cells.

As used herein, the phrases "nucleic acid sequence" or "nucleic acid molecule" refer to an oligonucleotide, nucleotide or polynucleotide, fragments or portions thereof, and to DNA or RNA of genomic or synthetic origin which may be single- or double-stranded, and represent the sense or antisense strand. The definition of "antisense RNA" is an RNA sequence that is complementary to a sequence of bases in the corresponding mRNA. The RNA sequence is complementary in the sense that each base (or majority of bases) in the antisense strand (read in the 5' to 3' sense) is capable of pairing with the corresponding base (G with C, A with U) in the mRNA sequence read in the 5' to 3' sense. The definition "sense RNA" is an RNA sequence that is substantially homologous to at least part of the corresponding mRNA sequence.

In one embodiment, the nucleic acids are derived from a human papilloma virus (HPV) type 16 and/or type 18. The invention discloses a nucleic acid which can be a gene, a functional part of a gene (wherein a gene is a nucleic acid which can be expressed), a precursor of a gene, a transcribed gene on any nucleic acid level (i.e., DNA and/or RNA, or double- or single-stranded) and/or a gene product derived therefrom that can overcome cell, cycle suppression. The cell cycle suppression may be overcome by inactivating major tumor suppressor proteins, such as P53 and pRB (retinoblastoma) gene products, respectively, leading to loss of normal cellular differentiation and the development of a carcinoma. As used herein, the phrase "gene product" refers to mRNA or the polypeptide chain translated from an mRNA molecule, which in turn is transcribed from a gene. If the RNA transcript is not translated (e.g., rRNA, tRNA), the RNA molecule represents the gene product. As further used herein, the phrase "gene product" refers to any proteinaceous substance. The phrase "proteinaceous substance" herein refers to any molecule comprising peptide or protein.

In another embodiment, the invention discloses an alphavirus vector wherein the nucleic acid is derived from the human papilloma virus (HPV) type 16 and/or type 18, E6 and E7 oncogenes or functional fragments or derivatives thereof which are involved in transformation. The phrase "functional fragment or derivatives thereof" as used herein means that the subject signature sequence can vary from the reference sequence by one or more substitutions, deletions, or additions, the net effect of which will not result in a functional dissimilarity between the two sequences. It is known by those of ordinary skill in the art that as a result of degeneracy of the genetic code, a multitude of gene sequences, some bearing minimal homology to the nucleotide sequences of any known and any naturally occurring genes may be produced. The invention contemplates each and every possible variation of the nucleic acid that could be made by selecting combinations based on possible codon choices. These combinations are made in accordance with the standard triplet genetic code. All such variations are to be considered as being specifically disclosed. Thus, in one embodiment, a minimal fragment length would be 9 amino acids since this is the length of the average CTL-epitope. Vaccination with peptides of this length does indeed result in a CTL response. Further, constructs that encode longer peptides/proteins are also considered part of the invention such that the preparations are not limited by HLA-restriction.

The invention discloses an alphavirus vector system comprising nucleic acid derived from a human papilloma virus (HPV), wherein the nucleic acid encodes at least one antigenic polypeptide fragment of the HPV. The phrase "antigenic polypeptide fragment" as used herein refers to at least one gene product or fragment thereof derived from the HPV nucleic acid, wherein the gene product comprises a proteinaceous substance, wherein the proteinaceous substance is an antigen (i.e., a foreign invader which is usually a protein or protein attached moiety) capable of initiating an immune response. An "immune response" as used herein refers to the physiological response stemming from activation of the immune system by the antigen. In one embodiment, the immune response involves the production HPV-specific cytotoxic T lymphocyte (CTL).

The invention further discloses an alphavirus vector system comprising nucleic acid of a human papilloma virus (HPV) origin, wherein the nucleic acid encodes at least one antigenic polypeptide fragment of the HPV. The antigenic polypeptide fragment is derived from protein E6 and/or protein E7 of HPV. E6 and E7 are viral oncogenes. In one aspect, the gene product comprises an antigenic polypeptide fragment originating from E6 protein and/or E7 protein of HPV. E6 and E7 protein refer to oncoproteins derived from E6 and E7 HPV genes, respectively, and are viral associated products expressed in cervical cancer and can immortalize target cells. The expression of E6 and E7 genes is selectively maintained in pre-malignant and malignant cervical lesions, wherein their gene products contribute to the transformation process and are necessary to maintain the transformed state.

The invention also discloses an alphavirus vector system comprising nucleic acid originating from a human papilloma virus (HPV), wherein the nucleic acid encodes at least one antigenic polypeptide fragment of the HPV. In one aspect, the antigenic polypeptide fragment comprises one antigenic polypeptide fragment of E6 and one antigenic polypeptide fragment of E7. As used herein, "antigenic polypeptide fragment" of HPV herein refers to tumor antigens E6 and E7 that can bind to the cellular tumor suppressor products pRB and P53. In one aspect, the nucleic acid encoding E6 and E7 or fragments thereof is fused in frame.

The invention further discloses an alphavirus vector system comprising nucleic acid originating from a human papilloma virus (HPV), wherein the nucleic acid encodes at least one antigenic polypeptide fragment of the HPV. In this embodiment, the antigenic polypeptide fragment is at least partially deprived of the capacity to bind to pRb and/or P53 protein. The retinoblastoma (pRb) gene and the p53 gene encode tumor suppressor gene products that control cell proliferation. Loss of activity of the pRb and the p53 genes causes unrestrained cell growth.

E7 is a cytoplasmic serine phosphoprotein and has been shown to be a transcriptional transactivator and transforming protein. E7 binds Rb protein to form a complex that is presumably moved to the nucleus. E6 binds to a cellular protein called E6-Ap. This complex then binds to p53. E6-Ap is an ubiquitin ligase that is loaded with activated ubiquitin molecules by cellular enzymes, which are transferred to p53. Ubiquitin loading of p53 targets p53 for degradation by proteasome-mediated proteolysis. The forced entry of the cell into S-phase, in conjunction with genomic instability resulting from p53 degradation, may lead to malignancy.

E6/7 proteins from "low risk" HPV strains do not appear to associate with Rb and p53. Expression of E6/7 antisense constructs reduces cell growth indicating that E6/7 may not only participate in initiation, but may also maintain the proliferative and malignant phenotype. To overcome the risk of a cell infected with virus that expresses E6 and E7 surviving and becoming tumorigenic (immortalized), a risk associated with other vector systems (i.e., vaccinia virus) used in the prior art, the invention discloses a recombinant virus expressing E6 and E7 oncogenes, wherein the recombinant virus is devoid of the capacity to suppress the retinoblastoma (pRb) and 53 gene products. Thus, cells infected with the virus are maintained in a non-tumorigenic (or oncogenic) state.

Methods to reduce DNA-protein interaction and protein-protein interaction are known. These methods include, but are not limited to, protein engineering. As used herein, "protein engineering" refers to any biochemical technique by which novel protein molecules are produced. These techniques include the de-novo synthesis of protein by assembling functional units from different natural proteins and the introduction of small changes, such insertions, deletions and substitutions, in the nucleotide or protein sequence. A "deletion" is defined herein as a change in nucleotide or protein sequence in which one or more nucleotides or amino acid residues, respectively, are absent. An "insertion" or "addition" changes the nucleotide or protein sequence and results in the addition of one or more nucleotides or amino acid residues, respectively, as compared to the naturally occurring polypeptide(s). A "substitution" results from the replacement of one or more nucleotides or amino acids by different nucleotides or amino acids, respectively.

The invention further discloses an alphavirus vector system comprising a translational enhancer element. The alphavirus vector system including the translational enhancer element of the present invention helps overcome lower expression or improves expression of heterologous proteins when compared to virus vector systems obtained for structural viral proteins during a wild-type SFV infection. In this embodiment, the translational enhancer element comprises a viral capsid gene segment, such as from an alphavirus (e.g., Semliki Forest virus (SFV)). As used herein, the phrase "translational enhancer element" refers to a functional sequence segment from, for example, a prokaryote or a eukaryote, from a viral origin, etc., wherein the translational enhances element increases the utilization of promoters and functions in either orientation and in any location (i.e., upstream or downstream) relative to the promoter.

Another embodiment, the invention discloses enhancer elements, in general, that enhance heterologous protein synthesis of an alphavirus vector system. The effect of such enhancers is likely mediated by the mnRNA sequence acting in cis during initiation of protein translation. Further, the original location of the initiator AUG is important for such enhancer effect.

In another embodiment, the invention further discloses an alphavirus vector system wherein the alphavirus capsid and spike proteins are expressed from at least one nucleic acid molecule. The alphavirus capsid and spike proteins are viral structural proteins. The alphavirus system of the invention, such as a Semliki Forest Virus-based system, has enhanced biosafety over known viral-based systems. By splitting the capsid region, which contains a translational enhancer and spike protein region, into two independent RNA molecules and by co-transfecting a cell with these two independent RNA molecules and the SFV vector replicon, RNA recombination is negligible such that the production of replication-efficient viruses is also negligible. Further, by abolishing autoprotease activity of the capsid protein, the alphavirus vector system has is safer and prevents the production of replication-efficient viruses.

In another embodiment, the invention further discloses an alphavirus vector system wherein the alphavirus capsid and spike proteins are expressed from at least two independent nucleic acid molecules. Such vector systems as referred to above are commonly referred to as helper-2-system and 2-helper or split helper system.

The invention further discloses an alphavirus vector system wherein the alphavirus comprises Semliki Forest Virus (SFV) and the alphavirus vector system is the Semliki Forest virus (SFV) expression system. SFV belongs to the genus Alphavirus of the family of the Togaviridae. A full-length cDNA copy of the SFV viral genome has been cloned in a bacterial plasmid including a prokaryotic DNA-dependent RNA polymerase such that viral RNA can be transcribed in vitro. These RNA transcripts are fully infectious (i.e., introduction into cells suffices to initiate replication and a full infection cycle, resulting in virus formation).

The Semliki Forest virus (SFV) expression system disclosed herein allows for efficient expression of foreign coding sequences as part of the SFV RNA replicon. The SFV viral system is suited to safely induce cellular immune responses against oncoproteins such as HPV 16/18 E6 and E7. SFV is an RNA virus replicating in the cell cytosol so no risk of integration of the E6 and E7 genes in the cellular genome exists. Further, since SFV infection is cytolytic by apoptosis, no genetic information of E6 and E7 will likely persist for more than one week after injection. In addition, no other vector proteins are produced, besides small amounts of viral replicase.

Immune responses against the SFV vector itself did not inhibit boost responses by subsequent immunizations with the same vector which is a problem associated with other viral vector systems. As further explained in the detailed description, a full-length cDNA copy of the SFV viral genome has been cloned in a bacterial plasmid including a prokaryotic DNA-dependent RNA polymerase such that viral RNA can be transcribed in vitro. These RNA transcripts are fully infectious (i.e., introduction into cells suffices to initiate replication and a full infection cycle, resulting in virus formation). The Semliki Forest virus (SFV) expression system disclosed herein allows for efficient expression of foreign coding sequences as part of the SFV RNA replicon.

The invention further discloses an alphavirus vector system wherein the HPV comprises HPV16 and/or HPV18 and the alphavirus vector system comprises a Human papilloma virus (HPV)-based vector system. In a further aspect, a HPV vector system based on HPV types 16 and 18, which are more closely associated with the development of cervical carcinoma, is disclosed. Included are viral variants of all viral vector systems of the present invention.

The invention further discloses an alphavirus vector system or other viral vector systems wherein the nucleic acid further encodes a cytokine gene or functional fragment thereof. Cytokines are primarily involved in signaling between cells of the immune system. It is herein provided to use Granulocyte-Macrophage Colony-Stimulating-Factor (GM-CSF) and/or Interleukin 12 (IL-12). However, the cytokines IL-2, IL-6, IL-18, and others are also contemplated. It is herein also disclosed to use separate vector particles, for example SFV particles, encoding cytokines and SFV particles encoding eE6, 7. The particles do not necessarily act at the same time or site. By making separate particles, the preparations can be given separately (in time, route or dosage). The definition of "functional fragment" herein refers to a fragment (i.e., reference sequence) derived from the subject sequence (e.g., a cytokine gene) which may vary from the subject sequence by one or more substitutions, deletions, or additions, the net effect of which does not result in an adverse functional dissimilarity between the reference and the subject sequence.

The invention further discloses a cell comprising an alphavirus vector system(s) or other viral vector systems according to the invention. Methods to infect a target cell with a recombinant virus of the present invention are known. The invention further provides the incorporation of an alphavirus vector system(s) of the present invention and/or a cell infected with an alphavirus vector system(s) of the present invention for the preparation of a medicament. In one embodiment, the medicament is a pharmaceutical composition. Pharmaceutical compositions for the preparation of a medicament and methods of delivering the medicament having a recombinant alphavirus and/or a cell comprising the recombinant alphavirus of the present invention are disclosed herein. The invention further discloses treating cervical cancer with the medicament including the alphavirus vector system of the present invention.

The invention further discloses incorporating the alphavirus vector system(s) of the present invention and/or a cell(s) infected with an alphavirus vector system(s) or other viral vector systems of the present invention in a medicament or a pharmaceutical composition. In this aspect, the medicament is a vaccine. Vaccine compositions and methods to administer a vaccine to a patient are known. In another embodiment, the invention discloses a biosafe method to vaccinate against cervical cancer. The method includes providing an alphaviral vector system with a broad host range comprising nucleic acid encoding tumor antigens devoid of capacity to bind to the cellular tumor suppressor products pRB and P53 and capable of inducing a HPV-specific cytotoxic T lymphocyte (CTL) response against HPV-transformed tumor cells expressing tumor antigens. CTLs can destroy cells expressing foreign antigens through recognition of foreign peptides generated within the cell, transported to the cell surface and presented by histocompatibility complex (MHC) class I antigens. The CTLs are, thus, potentially powerful agents of tumor cell destruction.

The invention further discloses incorporating an alphavirus vector system(s) of the present invention and/or a cell(s) infected with an alphavirus vector system(s) or other viral vector systems of the present invention into a medicament. In this embodiment, the medicament may be used for treating cervical cancer. In one aspect, the recombinant alphaviruses comprise at least nucleic acid derived from HPV, such as HPV E6 and/or HPV E7 viral oncogenes, derived from HPV type 16 and/or 18. The recombinant alphavirus may be used to immunize the body against HPV type 16 and/or 18 for the treatment and prevention of cervical cancer.

The invention further discloses a method for treating or preventing cervical cancer comprising providing an individual with a medicament, or pharmaceutical composition, comprising an alphavirus vector system(s) of the present invention and/or a cell(s) infected with an alphavirus vector system(s) of the present invention for the preparation of the medicament or pharmaceutical composition. In this aspect, the medicament or pharmaceutical composition may be a vaccine for treating cervical cancer.

BRIEF DESCRIPTION OF THE DRAWINGS

FIG. 2 illustrates the intracellular localization of E7 in SFV-E6E7 infected BHK cells. BHK21 cells were infected with SFV-E6E7. After overnight incubation, the cells were stained using anti-HPV16 E6 or anti-HPV16 E7 antibodies. A: Immunofluorescent staining of SFV-E6E7-infected cells with anti-HPV16 E6, B: Immunofluorescent staining of SFV-E6E7-infected cells with anti-HPV16 E7. Magnification 40×.

FIG. 9 shows the cloning strategy used for the construction of SFV-enhE6, 7. Out of the pSFV3-E6E7, the E6 sequence was modified with an NcoI site at the 5' end and an EcoRI site at the 3' end. The E7 sequence was modified with an EcoRI site at the 5' end and a BamHI site at the 3' end by PCR. The 5' end of the capsid gene of SFV coding for the first 34 amino acid residues has been shown to contain a translational enhancer. This enhancer was cloned in a pSFV-helper-S1 construct by Smerdou and Liljestrom (J. Virol. 73, 1092–1098, 1999). In addition, the sequence of foot-and-mouse disease virus (FMDV) 2A autoprotease (17 amino acids) was inserted in frame between the translational enhancer and p62 (SFV envelope protein) in order to provide cleavage between the proteins. The sequence containing the translational enhancer and the FMDV A2 autoprotease was synthesized from pSFV-helper-S1, and by PCR BamHI and NcoI restriction sites were generated at the 5' and 3' end, respectively. The enh-FMDV A2 protease-, E6- and E7 fragments were cloned into the BamHI site of pSFV3, producing pSFV3-eE6,7. In the original plasmid, the HPV16 E6 and E7 genes are present in tandem, with a stop codon after the E6 gene. In pSFV3-eE6,7, one base pair is inserted between E6 and E7 and the stop codon TAA of E6 is changed in GAA. Thus, in pSFV3-eE6,7, the sequence encoding E6 and E7 is in frame and expresses a fusion product of E6 and E7.

FIG. 19 illustrates the nucleotide sequence (SEQ ID NO: 4) of construct enhE6, 7.

DETAILED DESCRIPTION

Figure 1:
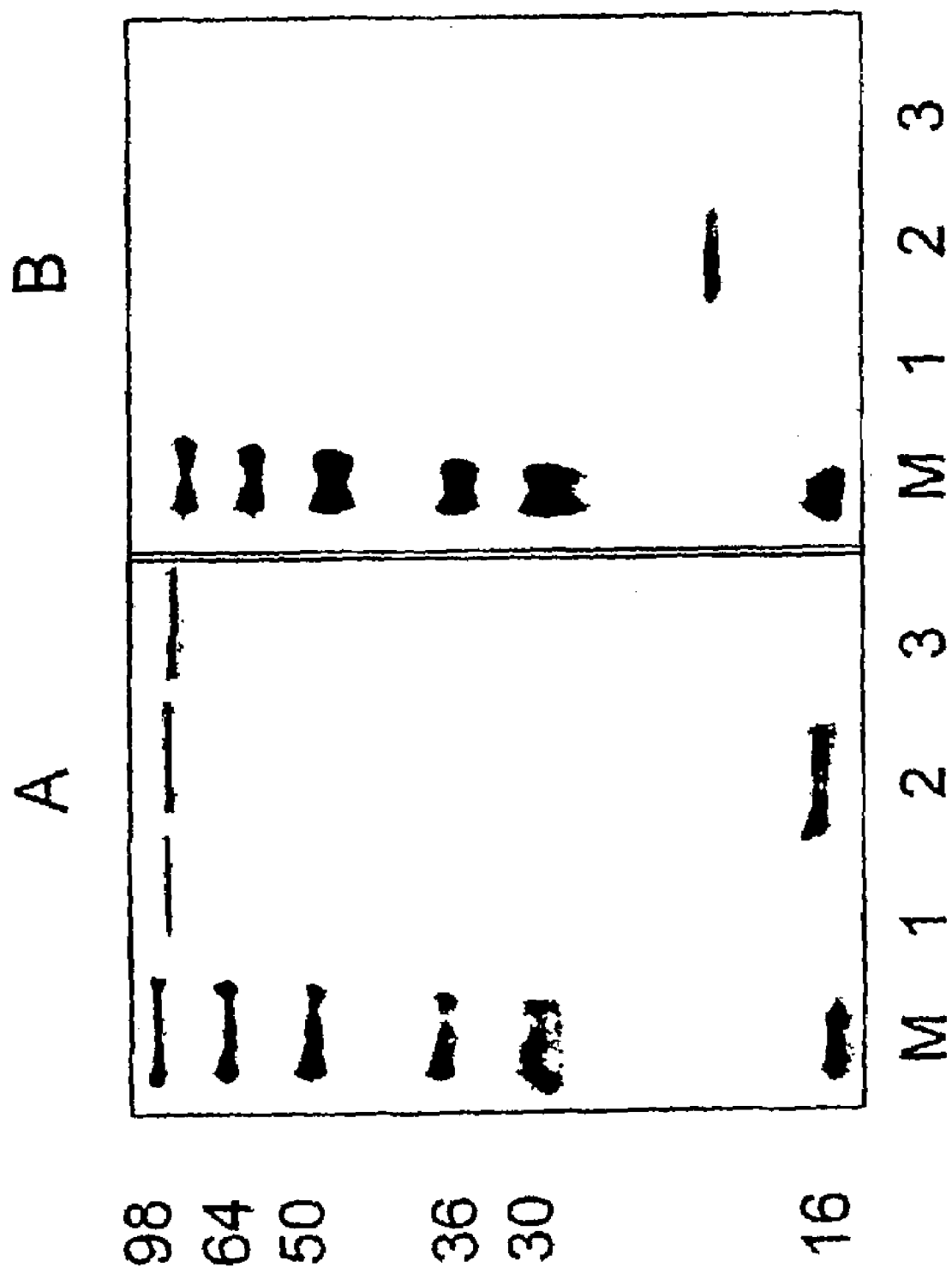
FIG. 1 is a Western blot analysis of SFV-E6E7 transfected BHK cell extracts. BHK cells were infected with SFV-E6E7 particles or SFV-LacZ particles. After overnight incubation, the cellular proteins were extracted and analyzed by SDS-PAGE and immunoblotting. E6 was detected using a polyclonal rabbit-anti-HPV16 E6 antibody (section A), E7 was detected using a monoclonal mouse-anti-HPV16 E7 antibody (section B). Lanes 1: BHK21 cells not infected; lanes 2: BHK21 cells infected with SFV-E6E7 particles; lanes 3: BHK21 cells infected with SFV-LacZ particles; M: protein marker

Genetic Immunization Against Cervical Carcinoma.

From molecular, clinical and epidemiological studies, it is evident that the high-risk human papilloma viruses HPV16 and HPV18 are linked to the development of precursor lesions of cervical cancer and invasive cervical carcinoma. The HPV genome encodes seven early (E) nonstructural regulatory proteins and two late (L) structural proteins. Integration of the viral DNA in the genome of the host cell, which is an essential step in HPV16- or HPV18-induced development of cervical carcinoma, results in a loss of E1- or E2-mediated transcriptional control. As a consequence, the transformed cells overexpress the E6 and E7 proteins and initiate the malignant transformation process.

Specific cell-mediated immunity is believed to play an essential role in the control of HPV infections and cervical carcinoma. This assumption is based on observations showing (i) that HPV-induced lesions regress spontaneously in the majority of individuals and (ii) that immunodeficient patients develop significantly more HPV-related proliferative lesions in skin and anogenital tissue than immunocompetent individuals. In several animal models, it has been demonstrated that the HPV E6 and E7 proteins, constitutively expressed in HPV-transformed cells, can act as targets for CTL-mediated tumor cell killing and stimulation of tumor-specific CTL activity.

Induction of an antigen-specific CTL response requires intracellular processing, of the target antigen and presentation of antigenic peptides by MHC class I molecules. This can be efficiently achieved with recombinant viral vectors. Heino P. et al. describes a method for the production of HPV16 virus-like particles (VLP's) in "Human papillomavirus type 16 capsid proteins produced from recombinant Semliki Forest virus assemble into virus-like particles." The VLP's include the two HPV16 structural proteins, L1 and L2. Upon expression of L1 and L2 in producer cell cultures, the cells generate VLP's.

In this disclosure, the Semliki Forest virus (SFV) vector system is used to express L1 and L2 in a producer cell with to generate HPV17 VLP's. The present invention discloses that HPV16 VLP's including L1 and L2 could be used as a vaccine for the induction of an antibody response against the virus HPV16. However, such a response would not be directed against HPV16-induced tumors since such tumors express the viral tumor antigens E6 and E7.

Boursnell M. E. G. et al. describes the construction and characterization of a recombinant vaccinia virus vector (TA-HPV) expressing the tumor antigens E6 and E7 from HPV16 or HPV18 in "Construction and characterization of a recombinant vaccinia virus expressing human papillomavirus proteins for immunotherapy of cervical cancer." It was demonstrated that the recombinant virus, upon intraperitoneal administration to mice, has the capacity to prime a cytotoxic T lymphocyte (CTL) response against cells infected with the same virus vector or sensitized with a synthetic E7 peptide epitope.

The alphavirus vector of the present invention has several distinct and important advantages over the TA-HPV vector. First, the alphavirus vector is replication-incompetent, whereas the vaccinia virus vector, which is based on attenuated live poxvirus, is replication-proficient. Replication-proficiency represents a major safety problem, the TA-HPV vectors carrying potentially oncogenic sequences derived from HPV16 or HPV18.

Second, vaccinia virus is a DNA virus, whereas alphaviruses are RNA viruses, which replicate and translate their RNA in the cytosol of cells without involvement of any nuclear processing. Therefore, genes encoded by an alphavirus vector cannot become integrated in the genome of the cell, whereas in the case of DNA virus vectors, this possibility can never be excluded. The exclusive cytosolic RNA processing of the genome of alphavirus vectors represents an important safety feature of these systems.

Third, the alphavirus vector of the present invention includes a translational enhancer in front of the antigenic sequence derived from HPV. This translational enhancer ensures high levels of antigen expression in target cells. Thus, the disclosed alphavirus vector is more efficient than the TA-HPV vector and induces higher levels of CTL activity with smaller dosages of virus.

European Patent Publication EP 0 711 829 A relates to one specific subcategory of alphavirus vectors, i.e., Sindbis virus vectors. The present invention discloses an alphavirus vector (derived from Semliki Forest virus) that encodes an antigenic sequence of a HPV. While it is indicated that foreign antigenic sequences may be included in the Sindbis-derived vector of the European Patent Application (many possibilities are mentioned, including sequences derived from an HPV), none of the examples in EP 0 711 829 involves expression of HPV-derived E6 and/or E7 antigenic sequences, but relates to expression of antisense sequences to E6 and/or E7. The present invention discloses an entirely different approach that is aimed at inhibition of E6 and/or E7 expression rather than stimulation of an immune response against E6 and/or E7, let alone induction of a cytotoxic T lymphocyte response using the Sindbis-derived vector of EP 0 711 829. Furthermore, the Sindbis-derived vector of EP 0 711 829 does not comprise a translational enhancer sequence.

PCT International Publication WO 99 28487 A (Crown in the right of the Queen; Khromykh; Varnavs) entitled "Flavivirus expression and delivery systems" discusses a flavivirus expression system. It does not involve alphavirus expression vectors since Flaviviruses comprise a different family of positive-strand RNA viruses, i.e., the Flaviridae. Alphaviruses belong to the family Togaviridae.

Borysiewicz L. K. et al. entitled "A recombinant vaccinia virus encoding human papillomavirus types 16 and 18, E6 and E7 proteins as immunotherapy for cervical cancer" describes the outcome of a first human clinical trial with a live recombinant vaccinia virus vector that expresses the E6 and E7 proteins of HPV16 and HPV18 (TA-HPV). The construction and characterization of the TA-HPV vector is described in Boursnell et al.

Berglund P. et al. entitled "Immunization with recombinant Semliki Forest virus induces protection against influenza challenge in mice" describes an immunization study in mice that utilizes the recombinant SFV vector system encoding the influenza virus nucleoprotein or *E. coli* LacZ. It does not relate to SFV encoding HPV-derived antigens.

The present invention discloses using the Semliki Forest virus (SFV) expression system. SFV belongs to the genus *Alphavirus* of the family of the Togaviridae. Alphaviruses include a nucleocapsid with one copy of a single-stranded RNA molecule surrounded by an envelope containing spike proteins. Alphavirus RNA has a positive polarity that enables the genomic RNA to initiate an infection when introduced into the cytoplasm of a cell. In addition, the RNA is self-replicating since it encodes its own replicase, and replication results in high-level expression of the viral proteins in host cells.

A full-length cDNA copy of the SFV viral genome has been cloned in a bacterial plasmid including a prokaryotic DNA-dependent RNA polymerase such that viral RNA can be transcribed in vitro. These RNA transcripts are fully infectious, i.e., introduction into cells can initiate replication and a full infection cycle to result in virus formation.

Liljeström and coworkers developed a vector system that allows for efficient expression of foreign coding sequences as part of the SFV RNA replicon. A high biosafety level is obtained by separating the replicase and structural genes of the viral genome. Thus, recombinant virus particles can be produced that infect cells only once. In addition, the SFV helper (containing the structural genes) was mutated in the gene encoding one of the spike proteins. In effect, such virus particles cannot infect cells unless they are activated with exogenous protease.

EXAMPLES

Example 1

The construction of recombinant SFV encoding HPV16 E6 and E7 and the cellular immune response in mice induced by these recombinant SF-E6E7 particles is disclosed. Infection of genital epithelial cells with human papillomavirus (HPV) types 16 and 18 is closely associated with the development of cervical carcinoma. The transforming potential of these high-risk HPVs depends on the expression of the E6 and E7 early viral gene products. Since the expression of E6 and E7 is selectively maintained in pre-malignant and malignant cervical lesions, these proteins are attractive candidates for immunotherapeutic and prophylactic strategies.

The construction, characterization and the in vivo immunotherapeutic potential of recombinant Semliki Forest virus (SFV) expressing the HPV16 E6 and E7 proteins (SFV-E6E7) is disclosed herein. Western-blot analysis and immunofluorescence staining demonstrated expression of E6 and E7 in BHK cells infected with SFV-E6E7. Immunization of mice with SFV-E6E7 resulted in an efficient in vivo priming of HPV-specific CTL activity. The induced CTLs lysed murine tumor cells transformed with the HPV16 genome and EL4 cells loaded with an immunodominant class-I-binding HPV E7 peptide. CTLs could reproducibly be induced by immunization with three injections of as few as $10^5$ infectious units of SFV-E6E7. Protection from tumor challenge was studied using the tumor cell line TC-1. Immunization with $5 \times 10^6$ SFV-E6E7 particles protected 40% of the mice from tumor challenge. These results indicate that E6E7 expression by the efficient and safe recombinant SFV system discloses a strategy for immunotherapy or immunoprophylaxis of cervical carcinoma.

Results.

Production and Titer Determination of SFV Particles.

Recombinant SFV particles were produced in BHK cells by electroporation of recombinant and Helper 2 RNA into these cells. After 24 hours, the medium containing the virus was removed from the cells and the virus particles were purified. Titers were determined by immunofluorescence using an antibody against SFV-nsP3 (replicase). This antibody was chosen because replicase is present in all cells infected with recombinant SFV. Thus, titers of different recombinant SFVs can be determined independent of the inserted foreign gene(s). Typically, titers of unpurified virus were $10^9$–$10^{10}$ infectious units/ml. After purification, titers were between $10^{10}$–$10^{11}$ infectious units/ml.

Western Blot Analysis of E6 and E7 Expression.

In order to verify that SFV-E6E7-induced expression of the recombinant E6 and E7 proteins, BHK cells were infected with SFV-E6E7 or SFV-LacZ serving as negative control. In FIG. 1, Western blots of cell lysates probed with anti-HPV16 E6 (panel A) or anti-HPV-16 E7 (panel B) are shown. Staining with the anti-E6 polyclonal antibody revealed a band with a $M_r$ of approximately 17 kDa. Staining with the anti-E7 monoclonal antibody revealed a band with an apparent electrophoretic mobility of approximately 20 kDa. This $M_r$ does not correspond to the calculated $M_r$ (11 kDa), but is in agreement with other studies in which E7 was produced by eukaryotic as well as prokaryotic expression systems.

Expression of HPV16 E6 and E7 in SPV-E6E7 Infected Cells.

Expression of E6 and E7 was also analyzed by indirect immunofluorescence analysis of BHK cells infected with SFV-E6E7. A low particle-to-cell ratio was chosen such that not all cells in the wells would become infected in order to visualize positive and negative cells within one microscopic field. As shown in FIG. 2, a strong fluorescence of both E6 and E7 was found in infected cells. In general, a bright staining of E6 was found in the perinucleus and cytoplasm while E7 was mainly found in the perinucleus. Previous studies demonstrated localization of the HPV18 E6 protein in the nuclear matrix and in non-nuclear membranes and of HPV16 E7 in the nucleus. However, it is likely that differences in staining pattern may be influenced by the amounts of proteins produced and the vector used for expression of the proteins.

HPV-specific CTLs Induced by Immunization of Mice With SFV-E6E7.

Figure 3:
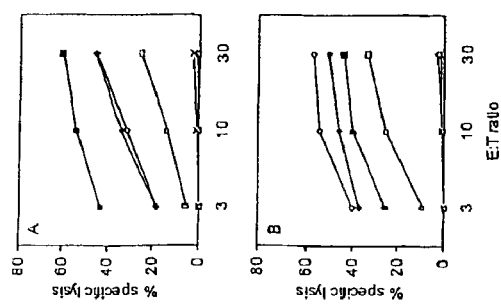
FIG. 3 shows the CTL activity induced upon immunization with SFV-E6E7 particles as determined after an 11 and 18 day in vitro restimulation. Mice were immunized s.c. and boosted twice (s.c. and i.p.) with purified $10^6$ SFV-E6E7 (n=4, open and closed squares and diamonds), SFV-LacZ particles (triangles) or PBS (crosses), as a control. CTL activity was determined one week after the last booster immunization. After 11 days (panel A) and 18 days (panel B) in vitro restimulation, the resulting effector cells were tested for cytolytic activity against 13-2 target cells in a triplicate well assay. The levels of cytolysis at different effector-to-target ratios are shown. The standard errors of the means of the triplicate determinations were always <10% of the value of the mean.

Mice were immunized s.c. and boosted twice (s.c. and i.p.) with $10^6$ purified SFV-E6E7, SFV-LacZ particles or buffer, as a control. CTL activity was determined one week after the last booster immunization. After 11 and 18 days of in vitro restimulation, the resulting effector cells were tested for their cytolytic activity against 13-2 target cells. As shown in FIG. 3, a strong CTL activity was induced upon administration of SFV-E6E7 particles (FIGS. 3A and 3B, squares and diamonds), whereas no HPV-specific CTL activity was induced upon immunization with SFV-LacZ particles or PBS (FIG. 3, triangles and crosses, respectively). The average level of cytolysis at day 11 (FIG. 3A) increased slightly upon prolonged in vitro restimulation, i.e., 18 days culture (FIG. 3B).

Figure 4:
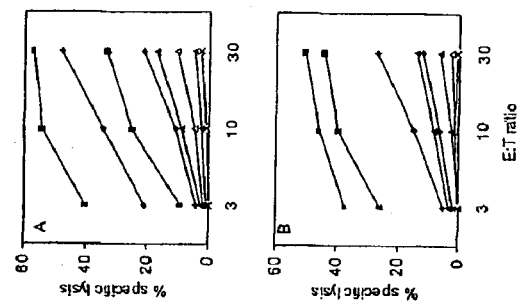
FIG. 4 illustrates the recognition and lysis of HPV16-transformed C3 cells as well as 13-2 cells expressing the $H-2D^b$-binding HPV16 CTL epitope by CTLs induced upon immunization with SFV-E6E7 particles. Mice were immunized s.c. and boosted twice (s.c. and i.p.) with purified $10^6$ SFV-E6E7 (n=2, squares and diamonds), SFV-LacZ particles (open triangles) or PBS (crosses), as a control. After 11 days in vitro restimulation, the resulting effector cells were tested for cytolytic activity against 13-2 target cells (panel A) and C3 cells (panel B) in a triplicate well assay. The levels of cytolysis at different effector-to-target ratios are shown. The standard errors of the means of the triplicate determinations were always <10% of the value of the mean.

Since 13-2 cells only express the MHC class I H-2D$^b$-binding CTL epitope of HPV16 E7 peptide 49-57 (RAHYNIVTF) (SEQ ID NO: 3), CTL clones directed against other epitopes on E6 and E7 are not detected. CTL activity against C3 cells as target cells, i.e., cells that express the entire HPV16 genome was also tested. CTLs present after 11 days of restimulation using C3 cells as stimulator cells, lysed 13-2 cells (FIG. 4A) and C3 cells (FIG. 4B) to the same extent. This result suggests that the HPV16 E7 peptide 49-57 is one of the dominant CTL epitope recognized by CTLs generated in C57BL/6 (H7-2$^b$) mice upon immunization with E6 and E7.

Figure 5:
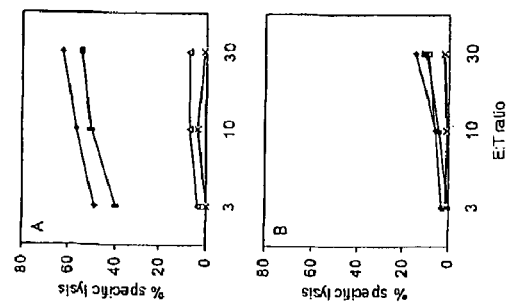
FIG. 5 illustrates the recognition of E7 49-57-loaded syngeneic EL4 cells by CTLs induced upon immunization with SFV-E6E7 particles. Mice were immunized s.c. and boosted twice (s.c. and i.p.) with purified $10^6$ SFV-E6E7 (n=2, squares and diamonds), SFV-LacZ particles (triangles) or PBS (crosses), as a control. After 18 days in vitro restimulation, the resulting effector cells were tested for cytolytic activity against E7 49-57-loaded EL4 cells (panel A) and unloaded EL4 cells (panel B) in a triplicate well assay. The levels of cytolysis at different effector-to-target ratios are shown. The standard errors of the means of the triplicate determinations were always <10% of the value of the mean.

This suggestion is supported by the observation that target cells loaded with HPV16 E7 49-57 were recognized and lysed to a very high level. FIG. 5A shows CTL activity, induced in two mice immunized with $10^6$ SFV-E6E7 particles, against EL4 cells loaded with the E7 49-57 peptide as targets. On the other hand, mice immunized with SFV-LacZ particles or PBS did not recognize peptide-loaded EL4 cells (FIG. 5A, triangles and crosses, respectively). In addition, unloaded EL4 cells were not recognized and lysed by these CTLs (FIG. 5B).

Figure 6:
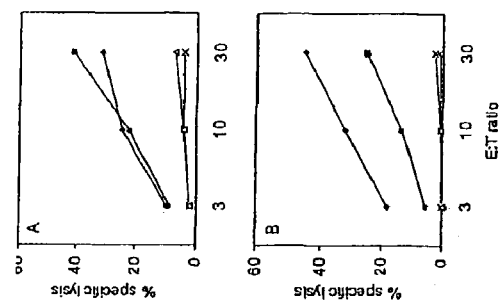
FIG. 6 shows the CTL activity in mice immunized with various doses of SFV-E6E7 particles. In two separate experiments, mice were immunized s.c. and boosted twice (s.c. and i.p.) with purified $10^4$ (solid triangles), $10^5$ (solid diamonds) or $10^6$ (solid squares) SFV-E6E7 particles, $10^6$ SFV-LacZ particles (triangles) or PBS (crosses), as a control. CTL activity was determined one week after the last booster immunization. After 18 days in vitro restimulation, the resulting effector cells were tested for cytolytic activity against 13-2 cells in a triplicate well assay. The levels of cytolysis at different effector-to-target ratios of two individual experiments are shown. The standard errors of the means of the triplicate determinations were always <10% of the value of the mean.

To determine the minimal effective dose of SFV-E6E7 particles, mice were immunized and boosted twice with $10^4$, $10^5$ or $10^6$ particles per immunization. In FIGS. 6A and 6B, the results of two separate experiments, each including two mice per injection dose, are given. In both experiments, immunization was performed with $10^6$ SFV-E6E7 particles (squares) and also with as few as $10^5$ particles (diamonds). All mice developed an HPV-specific CTL response. Immunization with $10^4$ particles (FIG. 6, solid triangles) resulted in a low, but detectable response in two out of four mice.

Antitumor Responses Induced by Immunization of Mice With SFV-E6E7 Particles.

Figure 7:
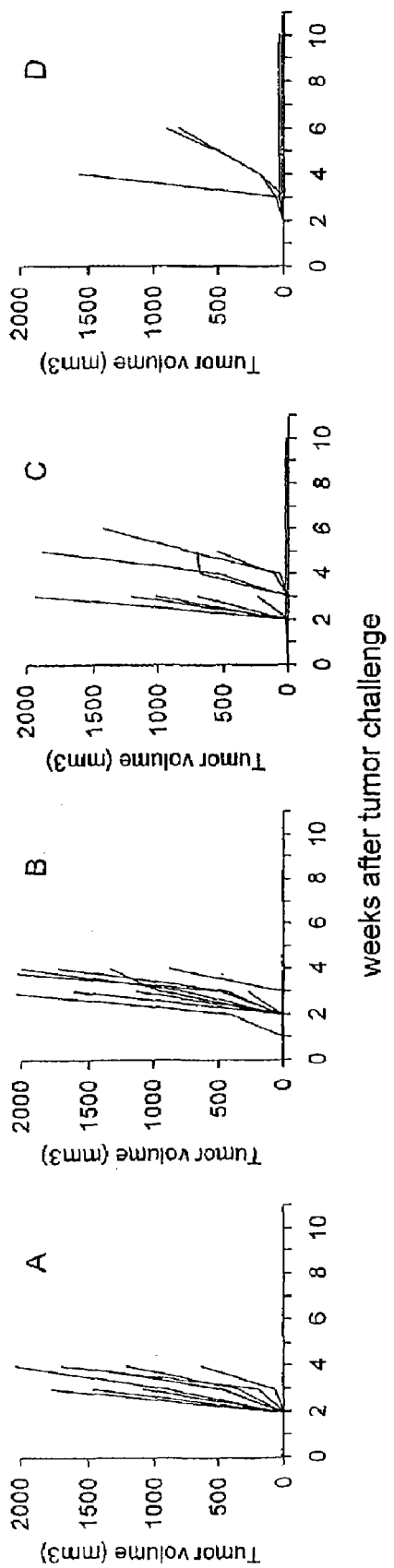
FIG. 7 illustrates the growth of TC-1 tumor cells in SFV-E6E7 immunized mice. Mice were immunized s.c. and boosted twice (s.c. and i.p.) with PBS (Panel A; n=10), $5\times10^6$ SFV-LacZ particles (Panel B; n=10), $10^6$ SFV-E6E7 particles (Panel C; n=10) or $5\times10^6$ SFV-E6E7 particles (Panel D; n=5). Tumor growth was monitored twice weekly. Each line represents the tumor volume of a separate mouse.
Figure 8:
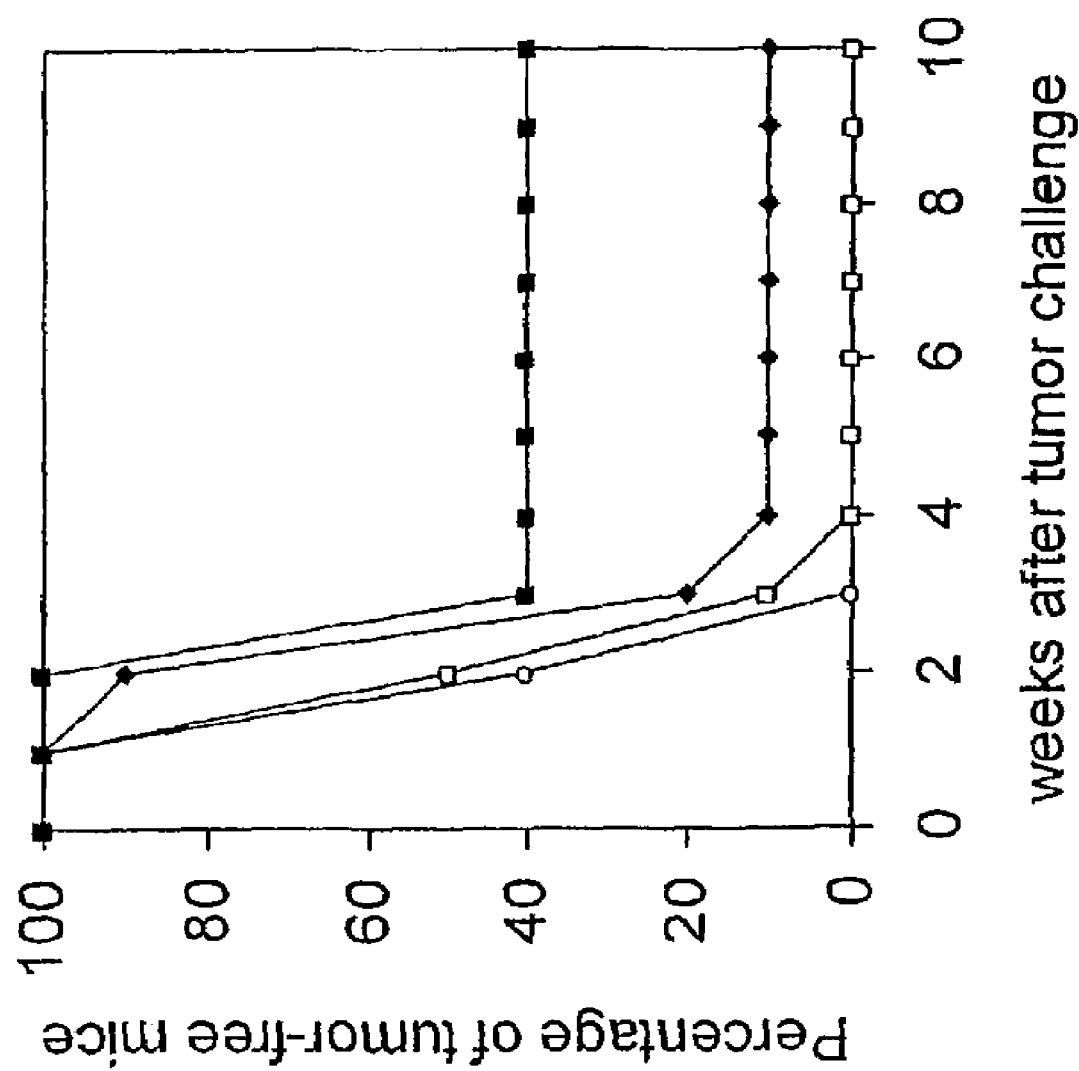
FIG. 8 illustrates the growth of TC-1 tumor cells in SFV-E6E7 immunized mice. Mice were immunized s.c. and boosted twice (s.c. and i.p.) with PBS (n=10; open circles), $5\times10^6$ SFV-LacZ particles (n=10; open squares), $10^6$ SFV-E6E7 particles (n=10; solid diamonds) or $5\times10^6$ SFV-E6E7 particles (n=5; solid squares). Tumor growth was monitored twice weekly. Shown are the percentages of mice with non-palpable tumors.

To examine whether recombinant SFV particles could generate protective immunity against a subsequent tumor challenge, mice were immunized and boosted with SFV-E6E7 particles and challenged s.c. with TC-1 cells, tumor cells expressing HPV16 E6E7. Tumor inoculation studies performed before initiating these immunization studies revealed that s.c. inoculation of $2\times10^4$ TC-1 cells reproducably induced tumors within two to four weeks after inoculation in all mice tested (n=15). FIGS. 7 and 8 show combined results of two separate immunization studies. Control mice, injected with PBS (n=10) or SFV-LacZ particles (n=10), developed palpable tumors within two to four weeks after tumor cell inoculation (FIG. 7, panels A and B, respectively; FIG. 8, open circles and open squares, respectively). Immunization with $10^6$ SFV-E6E7 particles (n=10) resulted in a delay in tumor onset in 50% of the mice as compared to control mice, with one out of ten mice not developing a tumor (FIG. 7, panel C; FIG. 8 diamonds). Upon immunization with a 5-fold higher dose of SFV-E6E7 particles, two out of five mice did not develop a tumor (FIG. 7, panel D; FIG. 8, closed squares). This example describes the construction, characterization and cellular immunotherapeutic potential of recombinant SFV particles encoding the early proteins E6 and E7 of HPV16.

Immunization of mice with SFV particles encoding HPV16 E6 and E7 resulted in a HPV-specific CTL response. Three injections of as few as 1 SFV particles sufficed for the induction of a CTL response in 50% of the mice, while three immunizations with $10^5$ SFV particles induced a HPV-specific CTL response in all mice tested. Increasing the dose to $10^6$ SFV particles per injection resulted in a reproducible CTL response with a high level of specific tumor cell lysis. In vitro blocking experiments with antibodies against CD4 and CD8 revealed that the lytic activity was due to CD8$^+$ T-cells, while no inhibition was found with anti-CD4 antibodies (not shown). Tumor challenge experiments demonstrated that immunization with $10^6$ SFV-E6E7 particles resulted in a delay in tumor onset while one of ten mice did not develop a tumor. Upon immunization with a 5-fold higher dose of SFV-E6E7 particles, 40% of the mice did not develop a tumor.

In the last few years, a number of peptide/protein-based or genetic immunization strategies have been described for the induction of HPV-specific CTL activity. Major drawbacks associated with a peptide-based approach include the problem of MHC-polymorphism and the risk of inducing T-cell tolerance rather than T-cell activation. Due to the induction of specific T-cell tolerance, vaccination with a tumor-specific peptide has been shown to result in an enhanced outgrowth of the tumor.

Immunization with larger proteins would overcome these problems, but requires efficient antigen delivery systems and/or safe adjuvants for efficient immune priming. Several groups have described the induction of HPV-specific CTL responses in mice upon immunization with recombinant vaccinia virus expressing HPV E6 or E7 or with syngeneic cells retrovirally transfected with the HPV E6 gene. In a phase I/II trial involving eight patients with late stage cervical cancer, vaccination with recombinant vaccinia virus expressing HPV18 E6 and E7-induced HPV-specific CTLs in one of three evaluatable patients. Potential drawbacks associated with the use of viral vector systems are immune responses against viral proteins in pre-immune patients (vaccinia virus) or integration of recombinant genes into the host cell genome (retrovirus). The potential drawbacks are especially important when the recombinant virus encodes oncoproteins, such as HPV E6 or E7, the risk of integration into the host cell genome is a point of major concern.

The SFV expression system was chosen which, apart from its transfection efficiency and high biosafety, would appear to be especially suited to safely induce cellular immune responses against oncoproteins such as HPV16 E6 and E7. First, since SFV is an RNA virus that replicates in the cell cytosol, the risk of integration of the E6 and E7 genes in the cellular genome is reduced. Moreover, SFV infection is cytolytic by apoptosis. Therefore, no genetic information of E6 and E7 will persist for more than one week after injection. In addition, no other vector proteins are produced besides small amounts of viral replicase. Berglund et al.

demonstrated that immune responses against the vector itself did not inhibit boost responses by subsequent immunizations with the same vector.

Recognition by the immune system of virally-infected cells or tumor cells occurs via virus- or tumor-specific antigenic peptides presented in the context of MHC class I molecules. Infection of cells with recombinant SFV particles results in the production of the recombinant protein within the cytoplasm permitting presentation of the recombinant protein via the conventional MHC class I presentation route. However, for the induction of tumor- or virus-specific CTLs, antigen presentation has to be accompanied by costimulatory signaling.

Costimulatory molecules are confined to professional antigen-presenting cells (APCs). Therefore, the CTL response induced upon immunization with SFV-E6E7 particles may occur through transfection of APCs in vivo. Alternatively, APCs may take up residues of other cells that have been transfected in a process of cross-priming. The uptake of debris from infected cells by APCs is expected to be very efficient since an SFV infection induces apoptotic cell death. Upon uptake of infected-cell material (exogenous antigen), the recombinant protein will be processed and presented by MHC class II molecules to activate CD4+ T-helper cells. In addition, dendritic cells and macrophages are able to present exogenous antigen in the context of MHC class I molecules for presentation to and activation of CD8+ T-cells.

Thus, both arms of the cellular immune system essential for the induction of an optimal immune response will be activated upon administration of recombinant SFV particles, thus eliciting a potent CTL response. Moreover, SFV immunization will introduce both class I and class II antigenic epitopes into one and the same the APC which has recently been demonstrated to be required for a full activation of APCs. As demonstrated by Zhou et al., immunization of mice with SFV particles encoding for the nucleoprotein of influenza virus not only induces influenza-specific CTL activity, but also a nucleoprotein-specific antibody response. This observation supports the hypothesis of cross-priming and indirect presentation of antigenic peptides.

It has been demonstrated that immunization of mice with recombinant SFV-E6E7 particles induces a potent CTL response against HPV-transformed tumor cells. This result, combined with studies showing the high efficacy of the SFV system for priming the immune system of mice, as well as primates, and the recent development of the extremely, safe two-helper system discloses that the essential steps towards the design of an effective immunization strategy for the treatment and prophylaxis of HPV-induced cervical carcinoma.

Materials and Methods.

Cell Lines.

Baby hamster kidney cells (BHK-21) were obtained from the American Type Culture Collection (# CCL-10). The cells were grown in GMEM (Life Technologies, Paisley, UK) containing 5% fetal calf serum (PAA Laboratories, Linz, Austria). C3 cells, 13-2 cells and TC-1 cells were provided by Dr. C. Melief and Dr. R. Offringa (Leiden University, The Netherlands). The C3 cell line was derived from C57BL/6 (H-$2^b$) embryonic cells transfected with a plasmid containing the complete HPV16 genome. The 13-2 cell line was generated from C57B1/6 (H-$2^b$) embryonic cells transfected with the E1-region of adenovirus type 5 in which the adenoviral E1A epitope SGPSNTPPEI (SEQ ID NO: 5) is replaced by a HPV16 E7 CTL epitope, AA 49-57 (RAHYNIVTF) (SEQ ID NO: 3) (R. Offringa, personal communication).

The TC-1 cell line was generated from C57B1/6 primary lung epithelial cells with a retroviral vector expressing HPV16 E6E7 plus a retrovirus expressing activated c-Ha-ras[25]. EL4 cells were provided by Dr. L. Leserman (Centre d'Immunologie de Marseille-Luminy, France). C3, 13-2, TC-1 and EL4 cells were grown in IMDM (Life Technologies) supplemented with 10% fetal calf serum. Both media contained penicillin and streptomycin (Life Technologies; 100 U/ml and 100 µg/ml, respectively).

Mice.

Specific pathogen-free female C57B1/6 mice (Harlan CPB, Zeist, The (Netherlands) were between six and ten weeks of age at the start of the immunization protocols.

Peptide.

The HPV16 H-$2D^b$ binding E7 peptide RAHYNIVTF (SEQ ID NO: 3) (residue (49-57) was synthesized and purified by Dr. J. W. Drijfhout (Academic Hospital Leiden, The (Netherlands). The peptide was analyzed by reverse phase HPLC and found to be over 90% pure.

Cloning of HPV16 E6 and E7 in pSFV3.

pSFV-Helper 2 and pSFV3 were provided by Dr. P. Liljeström (Karolinska Institute, Stockholm, Sweden). The HPV16 E6 and E7 genes were obtained from the plasmid pRSV-HPV16E6E7, which was provided by Dr. J. Ter Schegget (Free University, Amsterdam, The Netherlands). In this plasmid, the HPV16 E6 and E7 genes are present in tandem, with a stop codon after the E6 gene. Amplification of the E6E7 tandem gene was done by PCR using the following primers, written in 5' to 3' direction: GACG-GATCCAAAGAGAACTCCAATG (SEQ ID NO: 1) (E6 forward) and GAGAATTCGGATCCGCCATG GTAGAT-TAT (SEQ ID NO: 2). (E7reverse). The PCR product was digested with BamHI and cloned into the BamHI site of pGEM7Zf+. After sequence confirmation, the E6E7 fragment was cloned into the unique BamHI site of pSFV3, producing pSFV3-E6E7.

Production and Purification of Recombinant SFV Particles.

pSFV3-LacZ was a gift from Dr. P. Liljeström (Karolinska Institute, Stockholm, Sweden). The pSFV3-E6E7, pSFV3-LacZ and the pSFV-Helper 2 plasmids were isolated using the Qiagen midi plasmid purification kit and linearized by digestion with SpeI (Life Technologies). RNA was synthesized from the linearized DNA by in vitro transcription using SP6 RNA polymerase (Amersham Pharmacia Biotech. Inc., Piscataway, N.J., USA). Capping analogue was obtained from Life Technologies. Fifteen µg SFV3-E6E7 or SFV3-LacZ and 7.5 µg SFV-Helper 2 RNA were admixed and cotransfected into 8×$10^6$ BHK cells in 0.8 ml GMEM by electroporation using the Biorad Gene Pulser$^R$II (two pulses of 850 V/25 µF; Biorad, Hercules, Calif., USA). After pulsing, the cells were suspended in 10 ml GMEM and cultured for 36 hours at 37° C. and 5% $CO_2$. The medium, containing the SFV-E6E7 or SFV-LacZ particles was centrifuged twice in a JA 20 rotor, (Beckman, St. Paul, Minn., USA) at 1800 rpm (i.e., 40,000×g at $r_{max}$) to remove cells and cellular debris.

The SFV particles were purified on a discontinuous sucrose density gradient (2 ml of a 15% sucrose solution (w/v) and 1 ml of a 50% sucrose solution (w/v) in TNE-buffer (50 mM Tris-Cl, 100 mM NaCl, 1 mM EDTA, pH 7.4)). Virus was collected from the interface. Sucrose was removed from the virus solution by overnight dialysis against TNE-buffer. The virus suspension was concentrated approximately 10-fold (Centricon 30 filter; Millipore, Bedford, Mass., USA), quickly frozen in $N_2$ and stored in aliquots at −80° C.

Before use, SFV particles were incubated with 1/20 volume of α-chymotrypsin (10 mg/ml; Sigma Chemical Co., St. Louis, Mo., USA) for 30 minutes at room temperature to cleave the mutated spike proteins. Subsequently, α-chymotrypsin was inactivated by the addition of 0.5 volume of aprotinin (2 mg/ml; Sigma Chemical Co.).

Titer Determination of SFV Particles.

Recombinant SFV particles were titrated by serial dilution on monolayers of BHK cells. After infection and overnight incubation, the cells were fixed for 10 minutes in 10% acetone and stained using a polyclonal rabbit anti-replicase (nsP3) antibody (a gift from Dr. T. Ahola, Biocentre Viiki, Helsinki, Finland) as primary antibody and FITC-labeled goat-anti-rabbit IgG as a secondary antibody (Southern Biotech. Assoc., Birmingham, Ala., USA). Positive cells were counted and the titer was determined after correcting for the dilution factor and the dilution caused by the activation and the volume of particles added.

Analysis of E6 and E7 Expression by Western Blotting.

BHK cells were infected with SFV-E6E7 particles or as a control with SFV-LacZ particles. After overnight incubation, the cells were harvested and lysed in lysis buffer (50 mM Tris.Cl, 5 mM EDTA, 150 mM NaCl, 0.5% Triton X-100, pH 7.4). Cell-free extracts were analyzed by SDS-PAGE. The proteins were blotted onto PVDF membrane (Immobilon-P, Millipore Corp., Bedford, Mass., USA) and E6 and E7 were detected with a polyclonal rabbit-anti-HPV16 E6 antibody (a gift from Dr. I. Jochmus, Deutsches Krebsforschungszentrum, Heidelberg, Germany) and a monoclonal mouse-anti-HPV16 E7 antibody (Zymed Lab. Inc. South San Francisco, Calif., USA), respectively. After incubation with alkaline phosphatase-linked secondary antibodies, the blots were stained with nitroblue tetrazolium and 5-bromo-4-chloro-3-indolylphosphate (Sigma Chemical Co.).

Indirect Immunofluorescence Analysis of E6 and E7 in SFV-E6E7 Infected Cells.

In an eight-well culture chamber slide (Life Technologies), a monolayer of BHK cells was infected with SFV-E6E7. Fixation of the cells and staining was done as described for the immunofluorescence with anti-replicase, except for the antibodies used. As primary antibodies, anti-HPV16 E6 or anti-HPV16 E7, as mentioned above, were used. The secondary antibodies were FITC-labeled anti-rabbit IgG and anti-mouse IgG, respectively (Southern Biotechn. Assoc., Birmingham, Ala., USA).

Immunizations.

Mice were immunized subcutaneously (s.c.), intraperitoneally (i.p.) or intravenously (i.v.) and boosted twice with a two-week interval, with $10^4$ to $5\times10^6$ SFV-E6E7 particles. As negative controls, mice were injected with equal doses of SFV-LacZ particles or PBS.

CTL Assay.

Seven to 21 days after the last booster immunization, spleen cells were isolated and cocultured with irradiated (100 Gy) C3 cells in a ratio of 25:1, in 25 cm² culture flasks, placed upright. After one and two weeks in culture, cells were harvested and restimulated with irradiated naive spleen cells (30 Gy) and irradiated C3 cells in a ratio of 2:5:0.1 in 24-well plates in the presence of 4 IU of recombinant hIL2/ml (Strathmann Biotech GMBH, Hamburg, Germany).

Five days after the first and/or second restimulation, cells were harvested and a CTL assay was performed by a standard four hour $^{51}$Cr release assay in triplicate determinations. Target cells were labeled for one hour with 3.7 MBq $^{51}$Cr/$10^6$ cells in 100 μl medium ($^{51}$Cr was from Amersham, London, UK). EL4 target cells were loaded with the HPV16 E7 49-57 (RAHYNIVTF) (SEQ ID NO: 3) peptide by a one hour incubation of the cells in the presence of 15 μg/ml of peptide in 100 μl of culture medium before labeling the cells with $^{51}$Cr. The mean percentage of specific $^{51}$Cr release of triplicate wells was calculated according to the formula: % specific release={ (experimental release-spontaneous release)/(maximal release-spontaneous release) } cpm×100. The spontaneous $^{51}$Cr-release was always <15%. The standard errors of the means of the triplicate determinations were <10% of the value of the mean.

Tumor Challenge Experiments.

Mice were immunized and boosted as described above with $10^6$ to $5\times10^6$ SFV-E6E7 particles, SFV-LacZ particles or PBS. One week after the, last booster immunization the mice were challenged s.c. with $2\times10^4$ TC-1 cells suspended in 0.2 ml Hanks Buffered Salt Solution (Life Technologies). Tumor measurements were done by the same skilled technician. At a tumor volume of approximately 1000 mm³, the mice were sacrificed.

Example 2

Two recombinant SFV plasmids that contain a translational enhancer were generated. One plasmid encodes a fusion protein of E6 and E7 by inserting one base pair between E6 and E7 and by changing the stop codon of E6. The resulting plasmid is named pSFV3-eE6,7 (FIGS. 9 and 19). In the other plasmid, the translational enhancer is placed in front of the original E6E7 construct, pSFV3-eE6E7.

Western Blot Analysis of Protein Expression.

To verify that SFV-eE6,7-induced expression of a recombinant fusion protein of E6 and E7, while SFV-E6E7 induces expression of the separate E6 and E7 proteins, lysates of cells infected with SFV-E6E7 or SFV-eE6,7 were compared by Western blot analysis. In addition, lysates of cells infected with the construct in which the translation enhancer was cloned in front of the original E6E7 construct, i.e., SFV-eE6E7, were analyzed.

Figure 10:
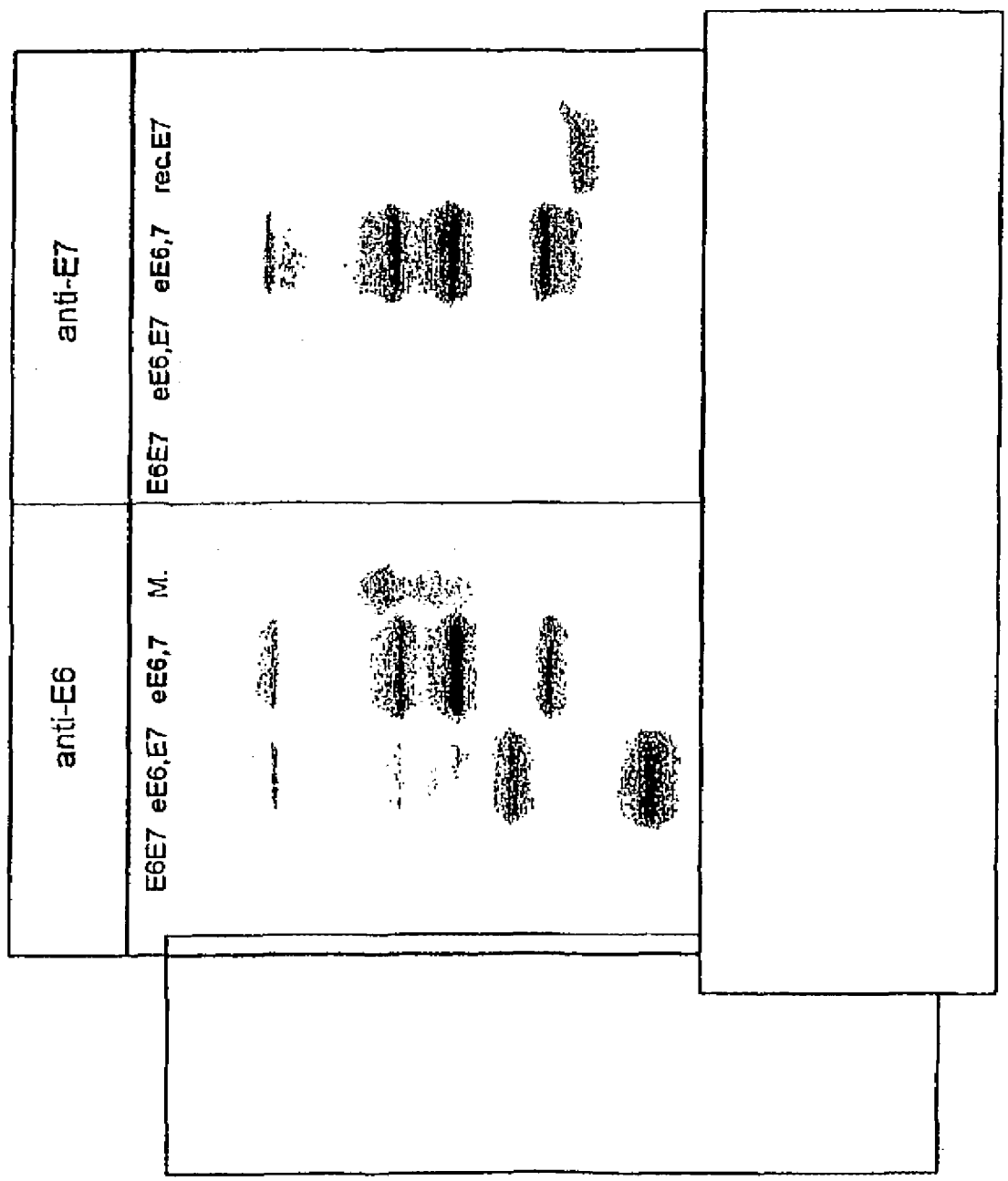
FIG. 10 illustrates a Western blot analysis of recSFV-transfected BHK cell extracts. BHK cells were infected with SFV-E6E7, SFV-eE6E7 or SFV-eE6,7 particles. After overnight incubation, the cellular proteins were extracted and analyzed by SDS-PAGE and immunoblotting. E6 was detected with a polyclonal rabbit-anti-HPV16 E6 antibody (lanes 1–3); E7 was detected with a monoclonal mouse-anti-HPV16 E7 antibody (lanes 5–8). Lanes 1 and 5: BHK21 cells infected with SFV-E6E7 particles; Lanes 2 and 6: BHK21 cells infected with SFV-eE6E7 particles; Lane 3 and 7: BHK21 cells infected with SFV-eE6,7 particles; Lane 4: protein marker (M); Lane 8: recombinant (*E. coli*) produced E7 protein.

In FIG. 10, Western blots probed with anti-HPV16 E6 or anti-HPV16 E7 are shown. Staining with both the anti-E6 and the anti-E7 antibody revealed three prominent bands in lysates from cells infected with SFV-eE6,7 (lanes 3 and 7), while no or very little E6 and E7 could be demonstrated upon infection with SFV-E6E7 (lanes 1 and 5). However, it should be noted that the procedure (amount of material and staining time) used for demonstration of the highly expressed fusion protein by Western blotting is not optimal for demonstration of the relatively low expression of E6 and E7 in SFV-E6E7 infected cell. In a previous study, expression of E6 and E7 could be demonstrated in cells infected with SFV-E6E7 using more material and a longer staining time.

The three major bands observed in the SFV-eE6,7 lysates had apparent electrophoretic mobilities of approximately 26 kDa, 36 kDa and 44 kDa, respectively. The 26 kDa band represents the fusion protein of E6 and E7 (17 kDa and 11 kDa, respectively). The bands of 36 kDa and 44 kDa, however, do not correspond to the calculated $M_r$'s of dimeric and trimeric complexes of the fusion protein. Nonetheless, since both bands stain positive with the anti-E6 antibody as well as with the anti-E7 antibody, the bands reflect a protein complex composed of both E6 and E7. In this regard, it should be noted that, it has been demonstrated that the $M_r$ of recombinant produced E7 protein (FIG. 10, lane 8) does not correspond to the calculated $M_r$ (11 kDa). Similarly, the apparent $M_r$'s of the bands may not reflect the actual $M_r$'s of the fusion proteins.

Staining the lysate from cells infected with SFV-eE6,E7 with the anti-E6 antibody revealed two bands of approximately 22 kDa and 32 kDa (FIG. 10, lane 2). Staining this lane with the anti-E7 antibody did not reveal a band (FIG. 10; lane 6) demonstrating that, as expected, only the E6 protein was translated in an enhanced fashion. The 22 kDa band observed in the ant-E6 blot is slightly higher than the calculated $M_r$ of E6, i.e., 17 kDa. The 32 kDa band might represent a dimeric complex of E6.

Analysis of E6 and E7 Expression by Pulse-labeling.

Figure 11:
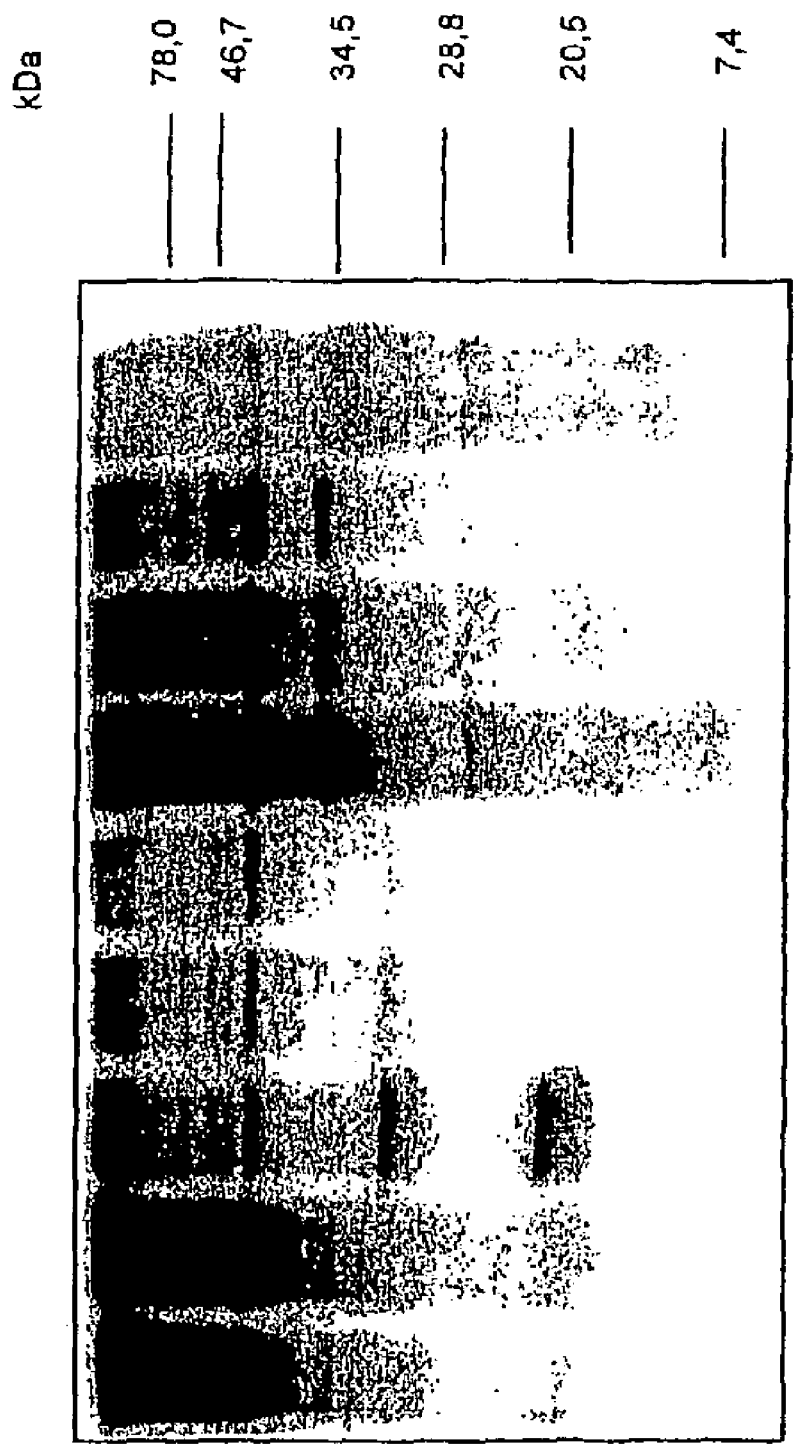
FIG. 11 shows the analysis of E6 and E7 expression by pulse labeling. BHK cells were infected with SFV-E6E7, SFV-eE6,E7 or SFV-eE6,7 particles. After six hours, the cells were cultured for an additional 30 minutes with methionine- and cysteine-free medium followed by a one-hour labeling period with $^{35}$S-methionine/cysteine. After one hour, the cells were washed and harvested or cultured for an additional 6, 16 or 40 hours before harvesting. Cell lysates were analyzed by SDS/PAGE and autoradiography. Lane 1: BHK21 cells not infected, analyzed after a six hour chase; Lane 2: BHK21 cells infected with SFV-E6E7, analyzed after a six hour chase; Lanes 3–5: BHK cells infected with SFV-eE6E7, analyzed directly or after a six hour or a 16 hour chase, respectively; Lanes 6–9: BHK21 cells infected with SFV-eE6,7, analyzed directly or after a six hour, a 16 hour or a 40 hour chase, respectively.

Production and stability of E6, E7 and the fusion protein E6,7 by BHK cells transfected with SFV particles was analyzed by pulse-chase-labeling of the cells with $^{35}$S-methionine/cysteine. As shown in FIG. 11 (lane 6), infection of BHK cells with SFV-eE6,7 particles and radiolabeling for one hour resulted in three prominently labeled bands of the E6,7 fusion protein. These bands correspond to the bands revealed on the Western blots. Although it may seem as if the 44 kDa band is also present in the control lysates, closer examination reveals that this upper fusion protein band in lanes 6–9 runs slightly lower than the band in lanes 1–5. The bands of 36 and 46 kDa are still present after a 6- and 16-hour chase period. Even after a 40-hour chase period, both bands, although less bright, are visible. The short exposure time that sufficed to visualize the enhanced fusion proteins could not reveal the bands of the E6 and E7 proteins produced upon infection with SFV-E6E7 either following a six-hour chase period (FIG. 11; lane 2) or directly upon labeling (not shown). Previously, it was demonstrated that a longer exposure time of the film is needed to visualize these proteins.

Autoradiography of lysates from cells infected with SFV-eE6E7 directly after labeling (FIG. 11, lane 3) revealed the same bands as those observed by Western blot analysis, i.e., a 22 and a 32 kDa band. However, in contrast to the enhanced fusion protein, within a six-hour chase period, most of the E6 protein was degraded. After 16 hours, the protein was degraded almost completely.

HPV-specific CTLs Induced by Immunization of Mice With SFV-eE6,7 and SFV-E6E7.

Figure 12:
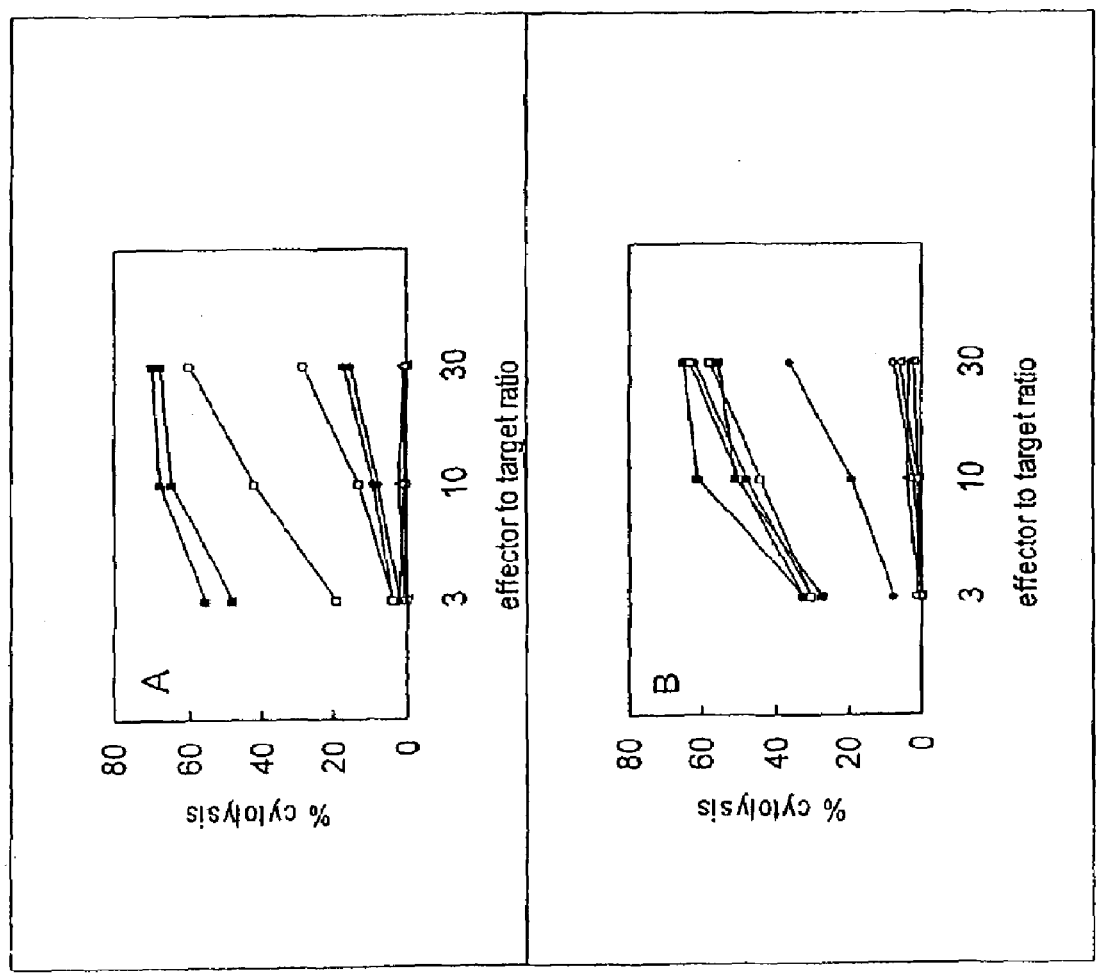
FIG. 12 illustrates the CTL activity induced upon immunization with SFV-E6E7 particles as determined after a seven and 14 day in vitro restimulation. Mice were immunized s.c. and boosted twice (s.c. and i.p.) with purified $10^6$ SFV-eE6,7 (n=2, closed squares), $10^5$ SFV-eE6,7 (n=2, open squares), $10^6$ SFV-E6E7 (n=2, closed circles), $10^5$ SFV-E6E7 particles (n=2, open circles) or with $10^6$ SFV-LacZ (n=2, closed triangles) or PBS (n=2, open triangles) as controls. CTL activity was determined one week after the last booster immunization. After seven days (panel A) and 14 days (panel B) in vitro restimulation, the resulting effector cells were tested for cytolytic activity against 13-2 target cells in a triplicate well assay. The levels of cytolysis at different effector to target ratios are shown. The standard errors of the means of the triplicate determinations were always <10% of the value of the mean.

Mice were immunized s.c. and boosted twice (s.c. and i.p.) with $10^6$ purified SFV-E6E7, SFV-eE6,7, SFV-eE6E7, SFV-LacZ particles or buffer, as a control. CTL activity was determined one week after the last booster immunization. After seven days (FIG. 12 A) and 14 days (FIG. 12 B) of in vitro restimulation, the resulting effector cells were tested for their cytolytic activity against 13-2 target cells and C3 target cells. Similar levels of cytolysis were induced against both cell lines. As shown in FIG. 12, spleen cells isolated from mice immunized with $10^6$, but also with as few as $10^5$ SFV-eE6,7 particles already displayed a high level of cytolysis in the short-term restimulation protocol (i.e., 7 days; FIG. 12 A). Upon immunization with $10^6$ SFV-E6,E7, significant levels of CTL activity could only be determined after long-term restimulation (FIG. 12 B). Short-term restimulation resulted in a very low level of CTL activity. Upon immunization with $10^5$ SFV-E6E7, no CTL activity was detectable. Immunization with SFV-eE6,E7 did not induce detectable levels of CTL activity against 13-2 cells nor against C3 target cells that express the entire HPV16 E6E7 genome (not shown).

Figure 13:
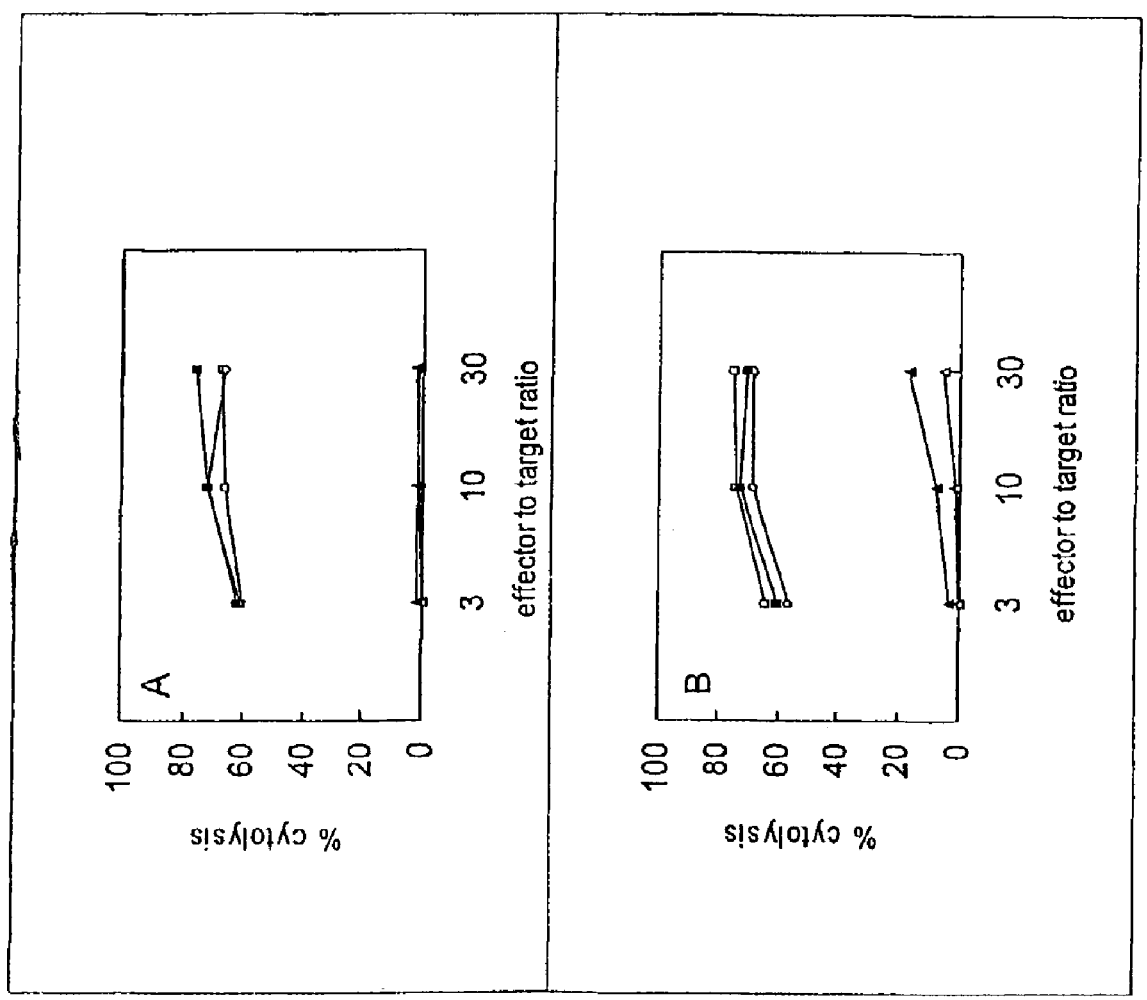
FIG. 13 shows the CTL activity induced upon immunization with 1, 2.5 and 5×$10^6$ SFV-eE67 particles. Mice were immunized s.c. and boosted twice (s.c. and i.p.) with purified 5×$10^6$ SFV-eE6,7 (closed squares), 2.5×$10^6$ SFV-eE6,7 (open circles), $10^6$ SFV-eE6,7 (open squares) or with 5×$10^6$ SFV-LacZ (closed triangles) or PBS (open triangles) as controls. CTL activity was determined 18 days (Panel A) or eight weeks (Panel B) after the last booster immunization. After seven days in vitro restimulation, the resulting effector cells were tested for cytolytic activity against 13-2 target cells in a triplicate well assay. The levels of cytolysis at different effector-to-target ratios are shown. The standard errors of the means of the triplicate determinations were always <10% of the value of the mean.

The level and maintenance of CTL activity induced upon administration of higher dosages of SFV-eE6,7 particles was also determined. Mice were immunized with 1, 2.5 or $5 \times 10^6$ SFV particles and CTL activity was determined 18 days and eight weeks after the last booster immunization. As shown in FIG. 13, the level of CTL activity induced with $10^6$ SFV-eE6,7 is presumably the maximal level of lysis that can be reached and detected in the bulk CTL $^{51}$Cr-release assay as immunization with 2.5 and $5 \times 10^6$ SFV-eE6,7 did not increase the percentage of specific lysis. Eight weeks after the last booster immunization, levels of cytolysis were as high as 18 days after the last booster (FIG. 13B and FIG. 13A, respectively).

For this bulk CTL assay, spleen cells are restimulated in vitro for several days resulting in proliferation of CTL precursors. Therefore, this assay is not a reliable assay to determine the actual frequency of CTL precursors that has been induced in vivo. To evaluate the number of CTL precursors, an HPV16 IFN-ã Elispot assay was performed. As demonstrated in Table 1, the number of CTL precursors 18 days after injection of 1, 2.5 and $5 \times 10^6$ SFV-eE6,7 particles was within the range of 1 in 1780 to 1 in 6600 total spleen cells. Since approximately 8% of the C57B1/6 spleen cells are CD8+ T-cells, 1 in 140 to 1 in 530 CD8-positive splenic T-cells is HPV-specific. Eight weeks after the last booster immunization, the level ranged between 1 in 430 to 1 in 1090 CD8$^+$ T-cells. Although no firm conclusions can be drawn from these numbers, since each dose and time point represents a single mouse, no correlation was observed between the dose injected and the level of specific CTLs.

In previous immunization protocols, mice were always immunized three times (i.e., one primary immunization followed by two booster immunizations). In order to determine the number of immunizations needed to induce a long-term response, mice were immunized once or twice and the level of CTL activity was determined at ten days, one month or three months after the last immunization.

Figure 14:
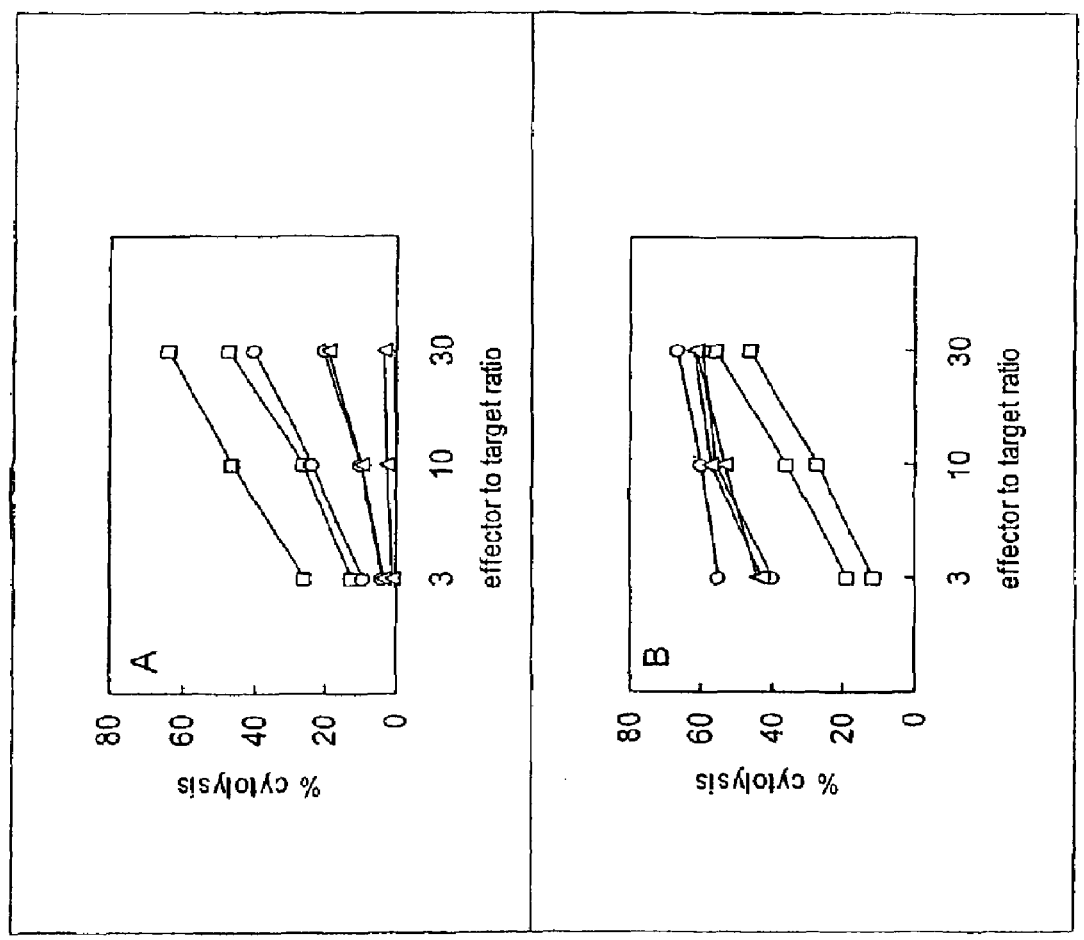
FIG. 14 illustrates how the induction of long-term CTL activity requires a single booster immunization. Mice received a single s.c. injection of 2.5×$10^6$ SFV-eE6,7 particles (Panel A) or two s.c. injections of 2.5×$10^6$ SFV-eE6,7 particles (Panel B). CTL activity was determined ten days (squares), one month (circles) or three months (triangles) after the (last) injection of particles. After seven days in vitro restimulation, the resulting effector cells were tested for cytolytic activity against 13-2 target cells in a triplicate well assay. The levels of cytolysis at different effector-to-target ratios are shown. The standard errors of the means of the triplicate determinations were always <10% of the value of the mean.

FIG. 14A shows that a single immunization of $2.5 \times 10^6$ SFV-eE6,7 particles induces a significant level of cytolysis at ten days after immunization (squares). This level gradually decreases in the next three months (one month: circles; three months: triangles). However, a single boost suffices to induce a significant CTL response up to three months after the booster immunization (FIG. 14B, triangles) which was as high as the response after one month (FIG. 14B, circles).

Figure 15:
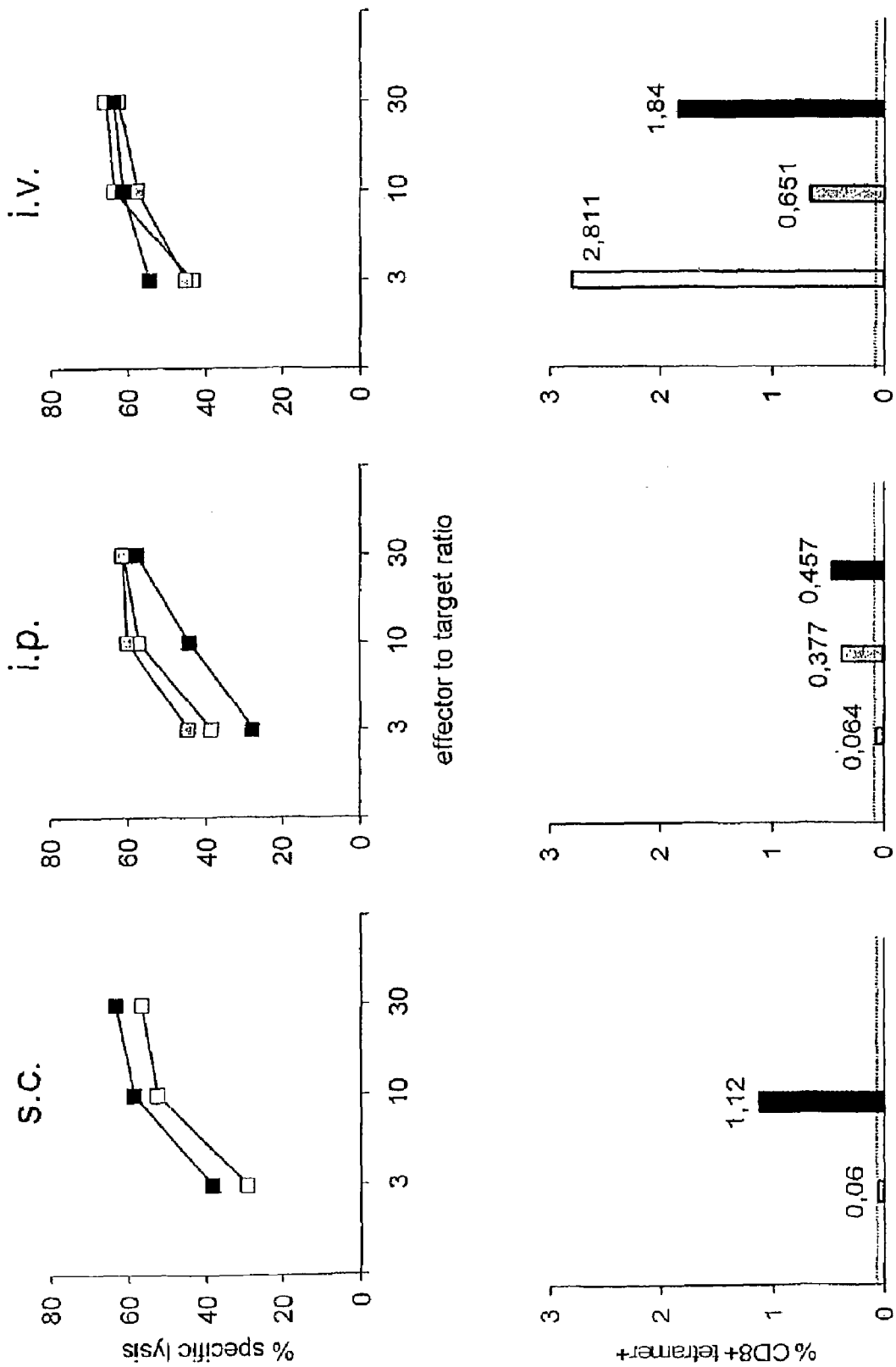
FIG. 15 illustrates the CTL activity and precursor CTL frequency in mice immunized with SFV-eE6,7 particles via different routes. Mice were immunized and boosted twice with purified $10^6$ SFV-eE6,7 particles s.c. (n=2), i.p. (n=3) or i.v. (n=3). Spleen cells were isolated one week after the last booster immunization. For CTL activity, spleen cells were restimulated for seven days in vitro. The resulting effector cells were tested for cytolytic activity against 13-2 target cells in a triplicate well assay. In the upper three panels, the levels of cytolysis at different effector-to-target ratios are given. For tetramer staining, spleen cells were stained directly after isolation with anti-CD8-FITC antibody and an HPV16-E7-specific MHC class I tetramer (PE-labeled). In the lower three panels, the percentages of CD8$^+$/tetramer$^+$ T-cells are given of the individual mice. The filled, grey and open bars in the lower panels correspond to the levels of CTL activity of the filled, grey and open symbols in the upper panels.

Finally, the immunization route was varied. Mice were immunized s.c., i.p. or i.v. with $1 \times 10^6$ SFV-eE6,7 particles. The bulk CTL assay shows that the levels of specific lysis by spleen cells isolated from the i.v. immunized mice (n=3) are slightly higher (at E:T ratio of 3 already near-maximal lysis) than those of mice immunized s.c. (n=2) or i.p. (n3) (FIG. 15, upper three panels). Separately, using the same spleen cells, CTL precursor frequencies were determined using HPV 16 E7-specific MHC class I tetramers. In the lower panels of FIG. 15, the percentages of tetramer$^+$/CD8$^+$ T-cells are given. The bars correspond to the CTL data in the upper panels. The relatively higher level of specific lysis observed upon i.v. immunization is also reflected in the number of tetramer$^+$/CD8+ T-cells.

Tumor Challenge and Re-challenge Upon Immunization of Mice With SFV-eE6, 7 Particles.

Figure 16:
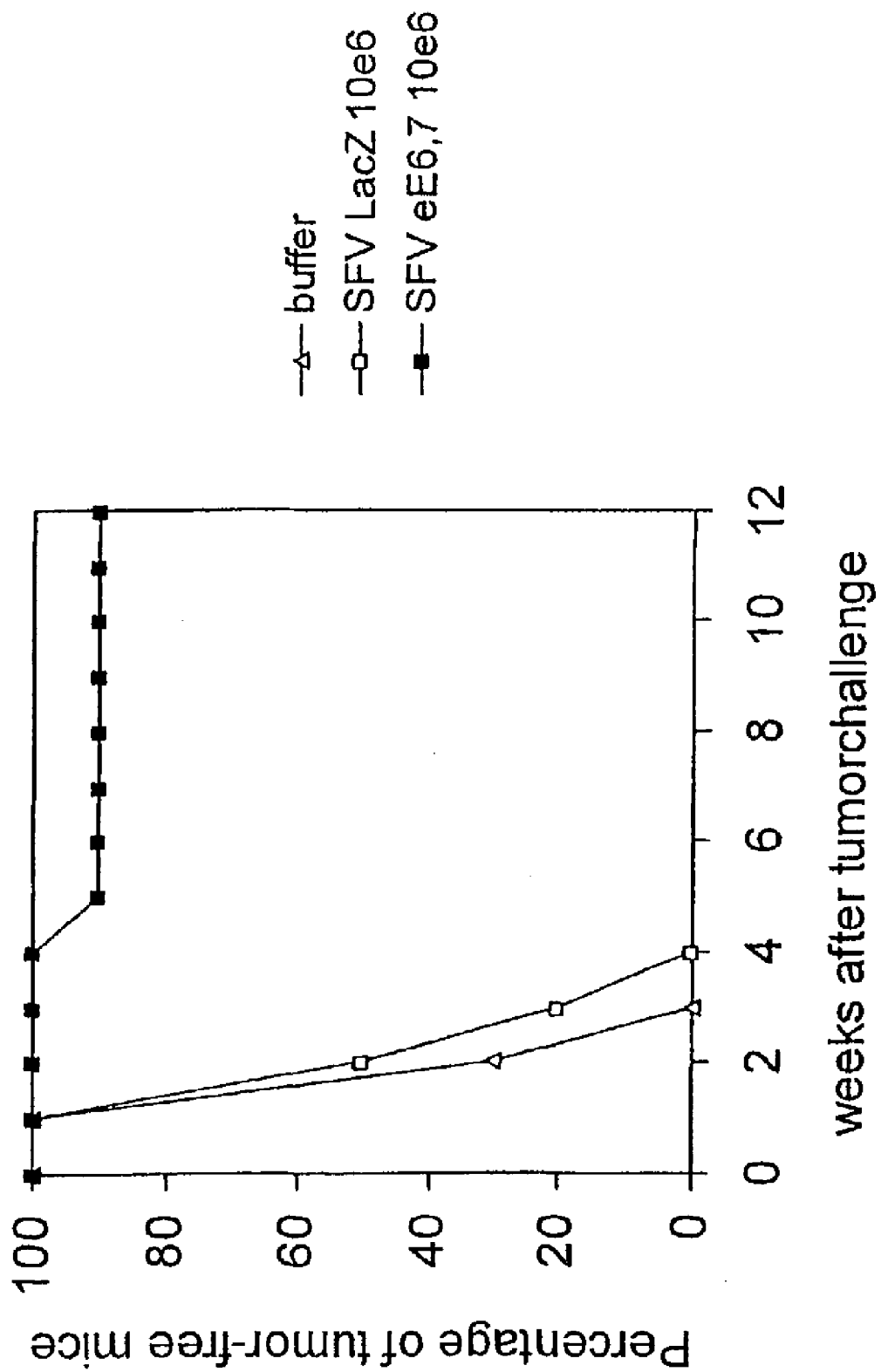
FIG. 16 shows protection from growth of TC-1 tumor cells in SFV-eE6,7 immunized mice. Mice were immunized s.c. and boosted twice (s.c. and i.p.) with PBS (n=10; open triangles), $10^6$ SFV-LacZ particles (n=10; open squares) or $10^6$ SFV-E6,7 particles (n=10; solid squares). Tumor growth was monitored twice weekly. The percentages of mice with non-palpable tumors in time are shown.

To examine whether recombinant SFV particles could generate protective immunity against a subsequent tumor challenge, mice were immunized and boosted with SFV-eE6,7 particles and challenged s.c. with TC-1 cells, tumor cells expressing HPV16 E6E7. FIG. 16 shows combined results of two separate immunization studies. Control mice, injected with PBS (n=10) or SFV-LacZ particles (n=10) developed palpable tumors within two to four weeks after tumor cell inoculation. In a previous study, it was demonstrated that immunization with $5×10^6$ SFV-E6E7 particles resulted in a partial tumor protection, i.e., two of five mice did not develop a tumor. Here it was demonstrated that immunization with $10^6$ SFV-eE6,7 particles protects nine out of ten mice from developing a tumor (FIG. 16). Immunization with a 5-fold higher dose ($5×10^6$ particles) protects four out of five mice (table 2).

To determine if long-term protection is induced, mice that did not develop a tumor were re-challenged s.c. with $2×10^4$ tumor cells at week 25 (exp. 1) or at week 13 (exp. 2) after the initial tumor challenge.

As shown in Table 2, all mice immunized with $5×10^6$ SFV-eE6,7 that did not develop a tumor at the initial tumor challenge were protected against the second tumor challenge 13 weeks later. Of the mice immunized with $10^6$ SFV-eE6,7, 50% and 60% did not develop a tumor upon a second tumor challenge at week 25 and week 13, respectively.

Tumor Treatment Upon Immunization With SFV-eE6,7 Particles.

Figure 17:
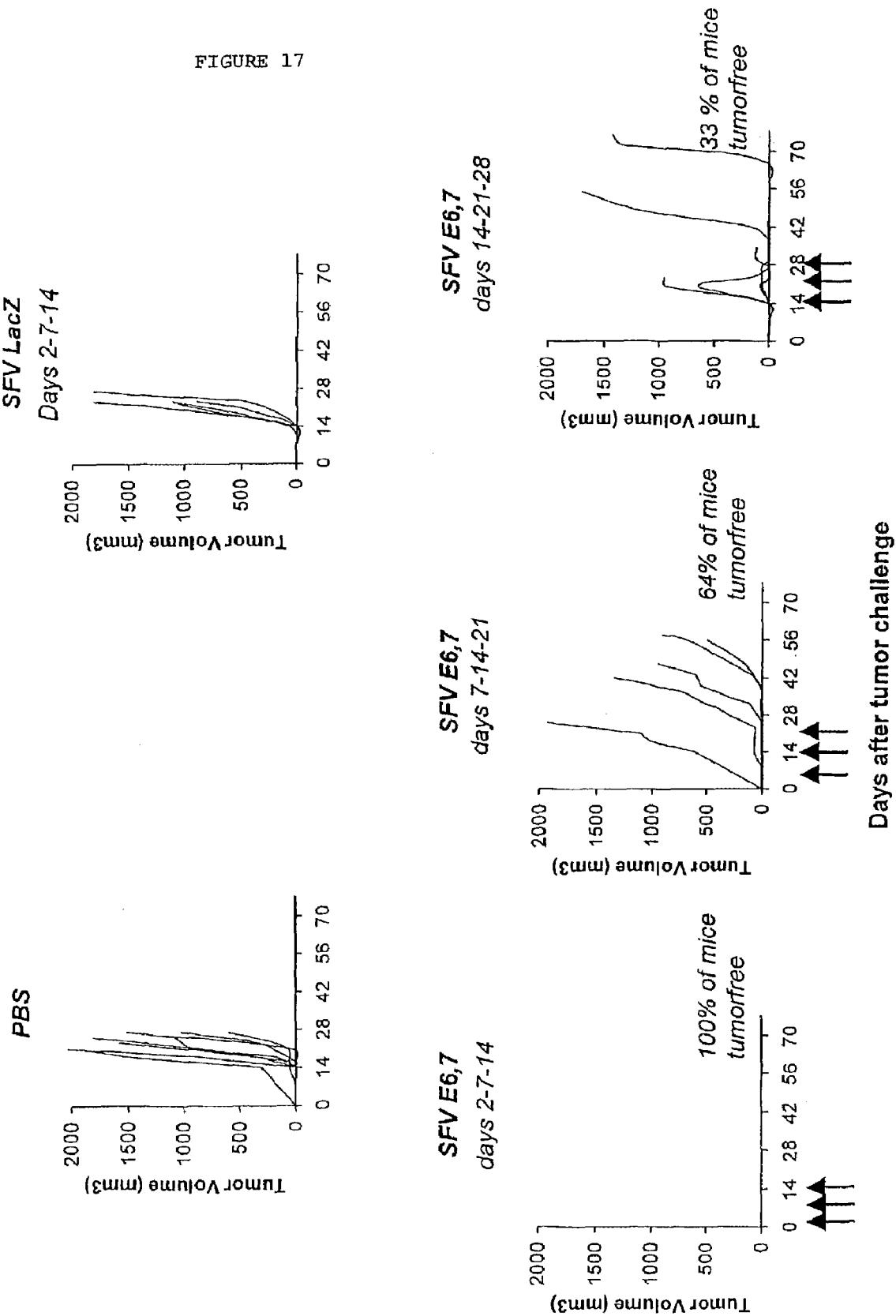
FIG. 17 illustrates therapeutic treatment of TC-1 tumors by SFV-eE6,7 immunization. Mice were inoculated s.c. in the neck with 2×$10^4$ TC-1. At several time points after tumor inoculation, mice were injected s.c. with 5×$10^6$ SFV-eE6,7 particles (lower three panels). One group of mice (n=7) was immunized on days two, seven and 14 after tumor inoculation, a second group (n=14) was immunized on days seven, 14 and 21 after inoculation. The last group (n=6) was immunized at days 14, 21 and 28 after inoculation. In addition, two control groups were injected with either PBS (n=9) or 5×$10^6$ SFV-LacZ particles (n=5) on days two, seven and 14 after tumor inoculation were included. Tumor growth was monitored twice weekly. Each line represents the tumor volume of a separate mouse. The combined results of two experiments are given.

The results obtained in the tumor challenge experiments as described above prompted a determination of the efficacy of SFV-eE6,7 immunization in a tumor treatment setting. Mice were inoculated s.c. with $2×10^4$ TC-1 cells. At several time points after tumor inoculation, mice were immunized s.c. with $5×10^6$ SFV-eE6,7 particles, SFV-LacZ or PBS. In FIG. 17 the tumor volumes of individual mice of two separate experiments are shown.

Figure 18:
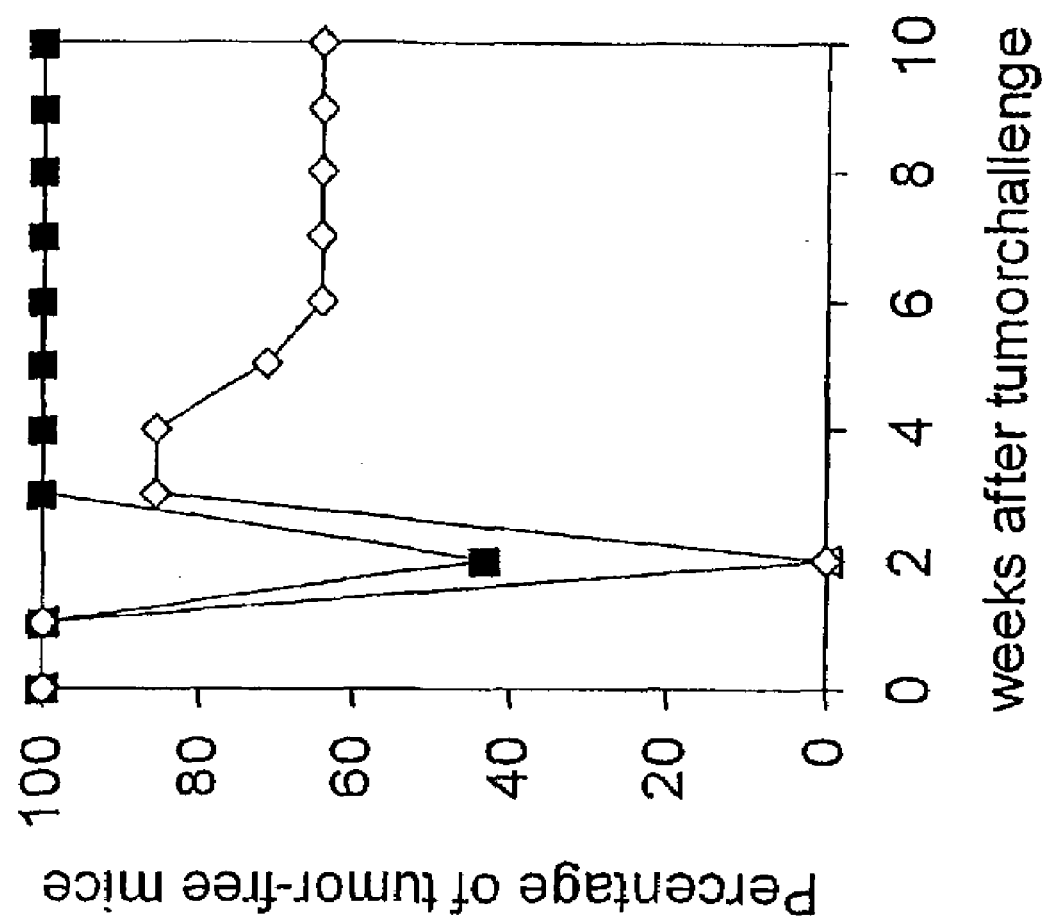
FIG. 18 illustrates therapeutic treatment of TC-1 tumors by SFV-eE6,7 immunization. Combined results of FIG. 17 showing the percentages of tumor-free mice in time. Mice were inoculated s.c. in the neck with 2×$10^4$ TC-1. At several time points after tumor inoculation, mice were injected with SFV-eE6,7 particles as described in the legend to FIG. 17. The percentages of tumor-free mice after injection of SFV-eE6,7 on days two, seven and 14 after tumor inoculation (n=7, filled squares), after injection of SFV-eE6,7 on days seven, 14 and 21 (n=14, open diamonds) or after injection with PBS (n=9, open circles) or 5×$10^6$ SFV-LacZ particles (n=5, open triangles) on days two, seven and 14 after tumor inoculation are shown. Tumor growth was monitored twice weekly.

FIG. 18 shows the combined results of these experiments as percentages of tumor free mice in time. Control and SFV-LacZ injected mice developed a tumor within two weeks after tumor inoculation. All mice immunized with SFV-eE6,7 particles on days two, seven and 14 after tumor inoculation were tumor free at day 100 -after tumor inoculation (FIG. 17, panel C). In four of seven mice of this group, a very small tumor was palpable at day 14 after tumor inoculation (FIG. 17). These tumor nodules disappeared within seven days and all mice remained tumor free.

In the second group of mice immunized with SFV-eE6,7 particles on days seven, 14 and 21 after tumor inoculation, all mice (n=14) in both experiments developed a small palpable tumor on day 14. In 12 of 14 mice, these nodules had disappeared on day 21. Ultimately, nine of 14 mice remained tumor free (FIG. 17). Finally, in one group of mice, immunization was initiated as late as day 14 after tumor inoculation. As shown in FIG. 17, 3 of 7 mice cleared the initial tumors. One of these mice cleared a tumor with a volume of 650 mm³ on day 20. One mouse again developed a tumor as late as 60 days after tumor inoculation.

Tumor Challenge and Re-challenge Upon S.C. Immunization With SFV-eE6,7 Particles.

Figure 20:
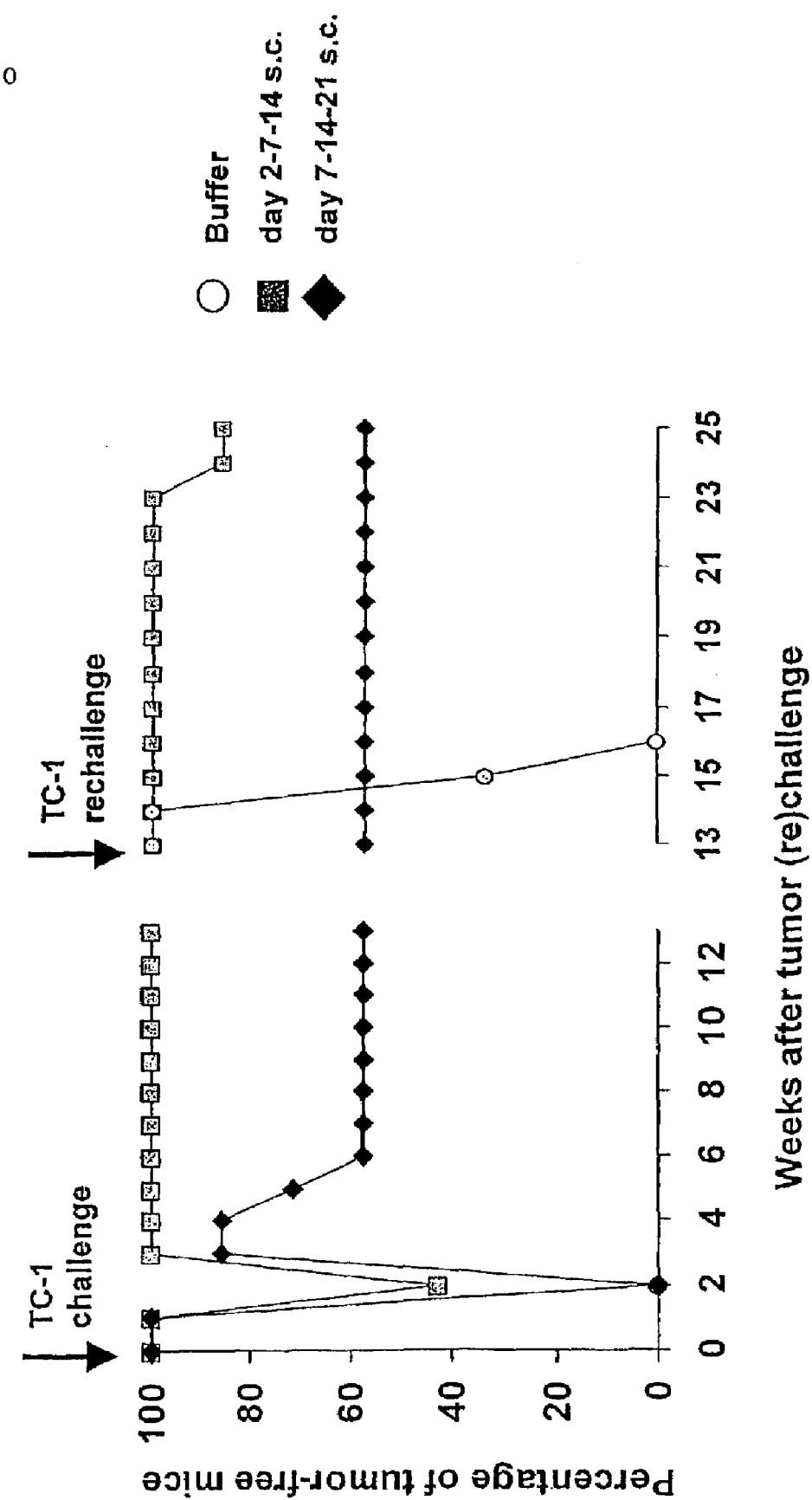
FIG. 20 illustrates tumor re-challenge of mice surviving a first tumor challenge. The left panel depicts the percentages of tumor-free mice in time of one of the experiments as shown and described in FIG. 17. Thirteen weeks after the first tumor inoculation, mice were re-challenged with 2×10⁴ TC-1 without additional immunization. The right panel shows the percentages of tumor-free mice upon tumor re-challenge of mice originally immunized with SFV-eE6,7 on days two, seven and 14 (n=7, squares) or with SFV-eE6,7 on days seven, 14 and 21 (n=4, diamonds). Since all control mice had developed a tumor upon the first tumor challenge, four control mice were included in the re-challenge experiment (circles). Tumor growth was monitored twice weekly.

In one of the experiments described above, tumor-free mice were re-challenged with TC-1 cells without additional immunization, 13 weeks after the initial tumor inoculation. Since none of the control mice were tumor-free after 13 weeks, four control mice were included in the experiment at the time of the second tumor inoculation. As shown in FIG. 20, all tumor-free mice immunized at days seven, 14 and 21 after the initial tumor inoculation remained tumor-free upon a second tumor challenge. In the group of mice immunized on days two, seven and 14, only one of seven mice developed a tumor after the second tumor inoculation.

Tumor Treatment Upon Intravenous Immunization With SFV-eE6,7 Particles.

Figure 21:
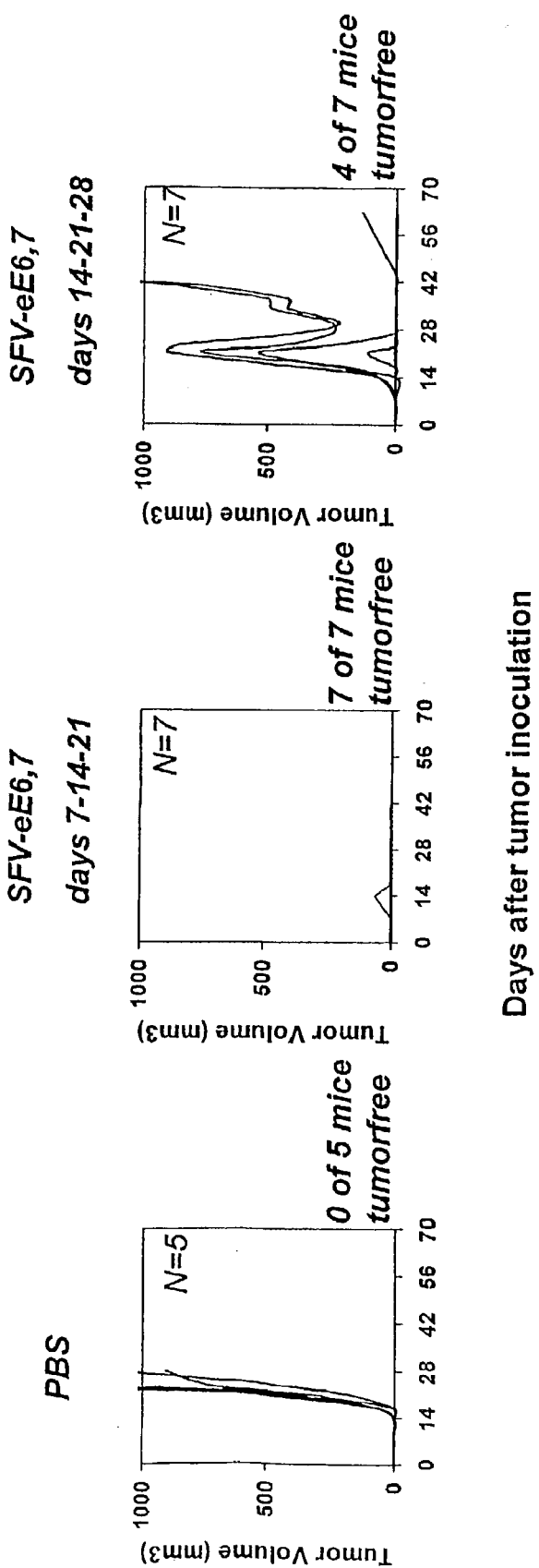
FIG. 21 shows therapeutic treatment of TC-1 tumors by intravenous immunization with SFV-eE6,7 particles. Mice were inoculated s.c. in the neck with 2×10⁴ TC-1. At several time points after tumor inoculation, mice were injected i.v. with 5×10⁶ SFV-eE6,7 particles or PBS. Mice were immunized on days seven, 14 and 21 (n=7; middle panel) after tumor inoculation or on days 14, 21 and 28 (n=7, right panel) after tumor inoculation. In addition, one buffer (PBS) control group was included (n=5, left panel). Tumor growth was monitored twice weekly. Each line represents the tumor volume of a separate mouse.

Elispot analysis and tetramer staining demonstrated that upon intravenous immunization, higher numbers of precursor CTLs are induced than after s.c. and i.p. immunization. Therefore, tumor therapy studies were performed in which mice were immunized intravenously. The experiments were performed similar to the experiments described above. As shown in FIG. 21, all mice immunized with $5×10^6$ SFV-eE6,7 particles on days seven, 14 and 21 after tumor inoculation, remained tumor-free. Even when immunization was initiated 14 days after tumor inoculation, a time-point at which all mice have developed a palpable tumor, all tumors regressed. Ultimately, four of seven mice eradicated the tumor completely and remained tumor-free thereafter.

Tumor Treatment Upon Intravenous Immunization With as Few as $5×10^4$ SFV-eE6,7 Particles.

Figure 22:
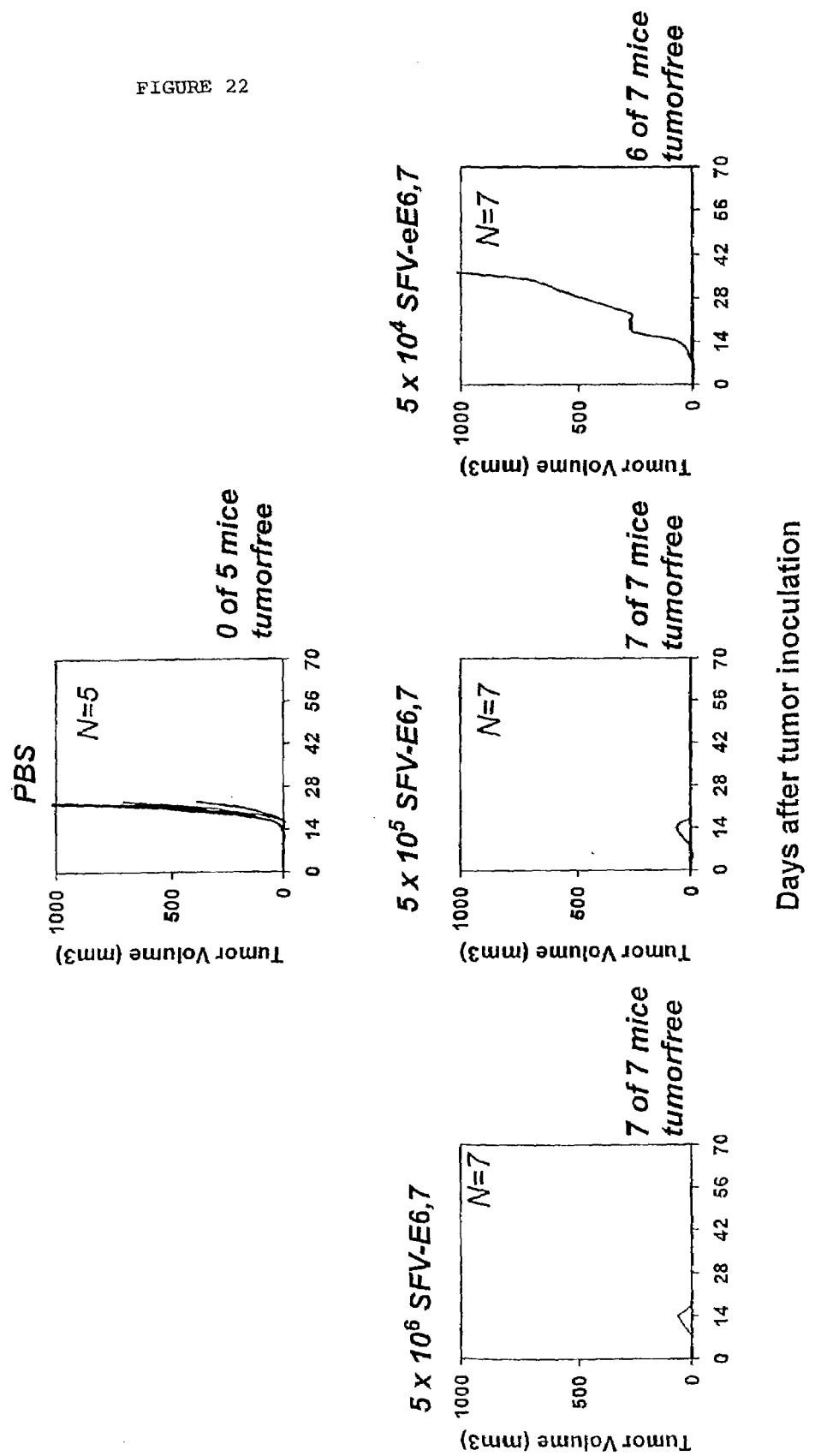
FIG. 22 illustrates therapeutic treatment of TC-1 tumors by intravenous immunization with decreasing amounts of SFV-eE6,7 particles. Mice were inoculated s.c. in the neck with 2×10⁴ TC-1. At several time points after tumor inoculation, mice were injected i.v. with 5×10⁶ SFV-eE6,7 particles (n=7; lower left panel), 5×10⁵ SFV-eE6,7 particles (n=7; lower middle panel), 5×10⁴ SFV-eE6,7 particles (n=7; lower right panel) or with PBS (n=5; upper panel) on days seven, 14 and 21 after tumor inoculation. Tumor growth was monitored twice weekly. Each line represents the tumor volume of a separate mouse.

To determine the minimal effective dose, mice were immunized with decreasing amounts of SFV-eE6,7 particles at days seven, 14 and 21 after tumor inoculation. As demonstrated in FIG. 22, all mice immunized with $5×10^5$ SFV-eE6,7 particles and six of seven mice immunized with as few as $5×10^4$ SFV-eE6,7 particles cleared the tumor and remained tumor-free up to ten weeks after tumor inoculation.

Materials and Methods.

Cell Lines.

Baby hamster kidney cells (BHK-21) were obtained from the American Type Culture Collection (# CCL-10). The cells were grown in GMEM (Life Technologies, Paisley, UK) containing 5% fetal calf serum (P.AA Laboratories, Linz, Austria). C3 cells, 13-2 cells and TC-1 cells were provided by Dr. C. Melief and Dr. R. Offringa (Leiden University, The Netherlands). The C3 cell line was derived from C57BL/6 ($H-2^b$) embryonic cells transfected with a plasmid containing the complete HPV16 genome. The 13-2 cell line was generated from C57B1/6 ($H-2^b$) embryonic cells transfected with the E1-region of adenovirus type 5 in which the adenoviral E1A epitope SGPSNTPPEI (SEQ ID NO: 5) is replaced by a HPV16 E7 CTL epitope, AA 49-57 (RAHYNIVTF) (SEQ ID NO: 3) (R. Offringa, personal communication). The TC-1 cell line was generated from C57B1/6 primary lung epithelial cells with a retroviral vector expressing HPV16 E6E7 plus a retrovirus expressing activated c-Ha-ras[25]. C3, 13-2 and TC-1 cells were grown in IMDM (Life Technologies) supplemented with 10% fetal calf serum. Both media contained penicillin and streptomycin (Life Technologies; 100 U/ml and 100 µg/ml, respectively).

Mice.

Specific pathogen-free female C57B1/6 mice (Harlan CPB, Zeist, The Netherlands) were between six and ten weeks of age at the start of the immunization protocols.

Construction of pSFV3-E6E7, pSFV3-eE6,7 and pSFV-eE6E7.

pSFV-Helper 2[16] amid pSFV3[15] were provided by Dr. P. Liljeström (Karolinska Institute, Stockholm, Sweden). The HPV16 E6 and E7 genes were obtained from the plasmid pRSV-HPV16E6E7[38], which was provided by Dr. J. Ter Schegget (Free University, Amsterdam, The Netherlands). In this plasmid, the HPV16 E6 and E7 genes are present in tandem, with a stop codon after the E6 gene. Amplification of the E6E7 tandem gene was done by PCR. The PCR product was digested with BamHI and cloned into the BamHI site of pGEM7Zf+. After sequence confirmation, the E6E7 fragment was cloned into the unique BamHI site of pSFV3, producing pSFV3-E6E7.

The plasmid pSFV3-eE6,7 was generated to express high levels of a fusion protein of HPV16 E6 and E7 by including a translational enhancer. The construction is depicted in FIG. 17 and as described as follows.

Out of the pSFV3-E6E7 the E6 sequence was modified with an NcoI site at the 5' end and an EcoRI site at the 3' end. The E7 sequence was modified with an EcoRI site at the 5' end and a BamHI site at the 3' end by PCR.

The 5' end of the capsid gene of SFV coding for the first 34 amino acid residues has been shown to contain a translational enhancer. This enhancer was cloned in a pSFV-helper-S1 construct by Smerdou and Liljeström (J. Virol. 73, 1092–1098, 1999). In addition, inserted sequence of foot-and-mouse disease virus (FMDV) 2A autoprotease (17 amino acids) was inserted in frame between the translational enhancer and p62 (SFV envelope protein) in order to provide cleavage between the proteins. The sequence containing the translational enhancer and the FMDV A2 autoprotease was synthesized from pSFV-helper-S1 and by PCR, wherein BamHI and NcoI restriction sites were generated at the 5' and 3' end, respectively. The enh-FMDV A2 protease-, E6- and E7 fragments were cloned into the BamHI site of pSFV3, producing pSFV3-eE6,7.

In the original plasmid, the HPV16 E6 and E7 genes are present in tandem with a stop codon after the E6 gene. In pSFV3-eE6,7 one base pair is inserted between E6 and E7 and the stop codon TAA of E6 is changed in GAA. Thus, in pSFV3-eE6,7 the sequence encoding E6 and E7 is in frame, expressing a fusion product of E6 and E7.

The construction of pSFV3-eE6E7 was done by cloning the intact E6E7 fragment and the translational enhancer-FMDV A2 autoprotease fragment in pSFV3-eE6E7. Since E6 and E7 are not in frame, it is to be expected that this plasmid encodes E6 in an enhanced fashion while translation of E7 is not enhanced.

The inserts encoding eE6E7 or eE6,7 were sequenced to verify that no modifications had been generated during the PCR.

Production and Purification of Recombinant SFV Particles.

pSFV3-LacZ[15] was a gift from Dr. P. Liljeström (Karolinska Institute, Stockholm, Sweden). The pSFV3-E6E7, pSFV3-eE6E7, pSFV3-eE6,7, pSFV3-LacZ and the pSFV-Helper 2 plasmids were isolated using the Qiagen midi plasmid purification kit and linearized by digestion with SpeI (Life Technologies). RNA was synthesized from the linearized DNA by in vitro transcription using SP6 RNA polymerase (Amersham Pharmacia Biotech. Inc., Piscataway, N.J., USA). Capping analogue was obtained from Life Technologies. Fifteen μg SFV3-E6E7 or SFV3-LacZ and 7.5 μg SFV-Helper 2 RNA were admixed and cotransfected into $8 \times 10^6$ BHK cells in 0.8 ml GMEM by electroporation using the Biorad Gene Pulser$^R$II (two pulses of 850 V/25 μF; Biorad, Hercules, Calif., USA). After pulsing, the cells were suspended in 10 ml GMEM and cultured for 36 hours at 37° C. and 5% $CO_2$. The medium containing the SFV-E6E7 or SFV-LacZ particles was centrifuged twice in a JA 20 rotor (Beckman, St. Paul, Minn., USA) at 1800 rpm (i.e., 40,000×g at $r_{max}$) to remove cells and cellular debris.

The SFV particles were purified on a discontinuous sucrose density gradient (2 ml of a 15% sucrose solution (w/v) and 1 ml of a 50% sucrose solution (w/v) in TNE-buffer (50 mM Tris-Cl, 100 mM NaCl, 1 mM EDTA, pH 7.4)). Virus was collected from the interface. Sucrose was removed from the virus solution by overnight dialysis against TNE-buffer. The virus suspension was concentrated approximately 10-fold (Centricon 30 filter; Millipore, Bedford, Mass., USA), quickly frozen in $N_2$ and stored in aliquots at −80° C.

Before use, SFV particles were incubated with 1/20 volume of α-chymotrypsin (10 mg/ml; Sigma Chemical Co., St. Louis, Mo., USA) for 30 minutes at room temperature to cleave the mutated spike proteins. Subsequently, α-chymotrypsin was inactivated by the addition of 0.5 volume of aprotinin (2 mg/ml; Sigma Chemical Co.).

Titer Determination of SFV Particles.

Recombinant SFV particles were titrated by serial dilution on monolayers of BHK cells. After infection and overnight incubation the cells were fixed for ten minutes in 10% acetone and stained using a polyclonal rabbit anti-replicase (nsP3) antibody (a gift from Dr. T. Ahola, Biocentre Viiki, Helsinki, Finland) as primary antibody and FITC-labeled goat-anti-rabbit IgG as a secondary antibody (Southern Biotech. Assoc., Birmingham, Ala., USA). Positive cells were counted and the titer was determined after correcting for the dilution, factor and the dilution caused by the activation and the volume of particles added.

Analysis of E6 and E7 Expression by Western Blotting.

BHK cells were infected with SFV-E6E7, SFV-eE6,7 or SFV-eE6E7 particles. After overnight incubation, the cells were harvested and lysed in lysis buffer (50 mM Tris.Cl, 5 mM EDTA, 150 mM NaCl, 0.5% Triton X-100, pH 7.4). Cell-free extracts were analyzed by SDS-PAGE. The proteins were blotted onto PVDF membrane (Immobilon-P, Millipore Corp., Bedford, Mass., USA) and E6 and E7 were detected with a polyclonal rabbit-anti-HPV16 E6 antibody (a gift from Dr. I. Jochmus, Deutsches Krebsforschungszentrum, Heidelberg, Germany) and a monoclonal mouse-anti-HPV16 E7 antibody (Zymed Lab. Inc., South San Francisco, Calif., USA), respectively. After incubation with alkaline phosphatase-linked secondary antibodies, the blots were stained with nitroblue tetrazolium and 5-bromo-4-chloro-3-indolylphosphate (Sigma Chemical Co.).

Analysis of E6 and E7 Expression by Pulse-labeling.

For pulse-labeling, BHK cells were infected with SFV-E6E7, SFV-eE6,E7 or SFV-eE6,7 particles. After six hours, the medium was removed, the plates were washed three times with phosphate-buffered saline (PBS) and the cells were cultured for an additional 30 minutes with methionine- and cysteine-free DMEM (ICN Biomedicals). At this time point, $^{35}$S-methioninetcysteine (0.37 MBq/well; Amersham) was added to the cultures. After one hour, the wells were washed free from radioisotope and harvested directly or cultured for an additional six, 16 or 40 hours before harvesting. At these time points, the cells were washed with PBS, (4° C.), harvested by scraping and resuspended in lysis buffer containing 0.2 mM phenyl-methane-sulphonyl-fluoride. After centrifugation, the supernatants of the cell lysates were analyzed by SDS/PAGE and autoradiography.

Immunizations.

Mice were immunized subcutaneously (s.c.), intraperitoneally (i.p.) or intravenously (i.v.) with $10^4$ to $5 \times 10^6$ recombinant SFV particles, followed by one or two booster immunization with a two-week interval or not boosted. As negative controls, mice were injected with equal doses of SFV-LacZ particles or PBS.

CTL Assay.

Seven days to three months after the last (booster) immunization, spleen cells were isolated and cocultured with irradiated (100 Gy) TC-1 cells in a ratio of 25:1, in 25 cm$^2$ culture flasks, placed upright. After one week in culture, cells were harvested and a CTL assay was performed by a standard four hour $^{51}$Cr release assay in triplicate determinations. Target cells were labeled for one hour with 3.7 MBq $^{51}$Cr/$10^6$ cells in 100 μl medium ($^{51}$Cr was from Amersham, London, UK). The mean percentage of specific $^{51}$Cr-release of triplicate wells was calculated according to the formula: % specific release={ (experimental release-spontaneous release)/(maximal release-spontaneous release) } cpm×100. The spontaneous $^{51}$Cr-release was always <15%. The standard errors of the means of the triplicate determinations were <10% of the value of the mean.

Initially, CTL analysis was also performed after an additional period of in vitro stimulation. For these experiments spleen cells cultured for one week, as described above, were harvested and restimulated with irradiated naive spleen cells (30 Gy) and irradiated C3 cells in a ratio of 2:5:0.1 in 24-well plates in the presence of 4 IU of recombinant hIL2/ml (Strathmann Biotech GMBH, Hamburg, Germany). Five days after restimulation, cells were harvested and a $^{51}$Cr-release assay was performed as described above.

Precursor CTL Frequency Determination by IFN-alpha Elispot Analysis.

Elispot analysis was done essentially according to the method described by Miyahira et al. (J. Immunol. Methods 181, 45054, 1995). In short, serially diluted, known numbers of freshly isolated spleen cells were plated into wells (96-well high affinity plates, Greiner) that had been coated overnight with purified anti-mouse-IFN-α mAb (Pharmingen, Calif.). Subsequently, 13-2 cells (only expressing the HPV16 E7 49-57 CTL epitope) were added for in vitro restimulation using effector to stimulator cell ratios of 1:1 to 4:1. In addition, spleen cells were cultured without stimulator cells as controls to determine antigen-independent IFN-α secretion. After overnight incubation, the wells were washed extensively and incubated with biotinylated anti-mouse IFN-α mAb (Pharmningen, Calif.). After one hour incubation at 37° C., the plates were washed and strepavidine-alkaline phosphatase was added. After one hour incubation at 37° C., the plates were washed and the spots were developed by adding the substrate BCIP (Sigma) in agarose. After overnight incubation at 4° C., the number of spots was determined using a stereomicroscope.

Precursor CTL Frequency Determination Using HPV-specific MHC Class I Tetramers.

Pycoerythrin (PE)-labeled HPV16 E7 49-57 MHC class I tetramers were provided by Dr. T. Schumacher (NKI, Amsterdam, The Netherlands). Freshly isolated spleen cells were stained with PE-labeled HPV16 E7 49-57 tetramer and FITC-anti-CD8 -(Pharmingen) for 20 minutes on ice followed by extensive washes with PBS containing BSA (0.5%) and NaN$_3$ (0.02%). Before FACS analysis, propidium iodide (PI) was added. Small lymphocytes were gated by forward and side scatter profiling.

Tumor Challenge Experiments.

Mice were immunized and boosted as described above with $10^6$ to $5×10^6$ SFV-E6E7, SFV-eE6,7 particles, SFV-LacZ particles or PBS. One week after the last booster immunization, the mice were challenged s.c. in the neck with $2×10^4$ TC-1 cells suspended in 0.2 ml Hanks Buffered Salt Solution (Life Technologies). Tumor measurements were done by the same skilled technician. At a tumor volume of approximately 1000 mm$^3$, the mice were sacrificed.

Tumor Treatment Experiments.

Mice were inoculated s.c. in the neck with $2×10^4$ TC-1 cells suspended in 0.2 ml Hanks Buffered Salt Solution (Life Technologies). At several time points after tumor inoculation, mice were immunized subcutaneously or intravenously with $5×10^4$ to $5×10^6$ SFV-eE6,7 particles. Mice were immunized on days two, seven and 14 after tumor inoculation, or on days seven, 14 and 21 after inoculation or finally on days 14, 21 and 28 after inoculation. In addition, control groups were included that were immunized with either PBS or $5×10^6$ SFV-LacZ particles on days two, seven and 14 after tumor inoculation. Tumor measurements were done by the same skilled technician. At a tumor volume of approximately 1000 mm$^3$, the mice were sacrificed.

TABLE 1

Precursor CTL frequency in SFV-eE6,7 immunized mice as determined by IFN-γ Elispot assay.

| Immunization | Dose | Evaluation time point | pCTL frequency total spleen[1] | pCTL frequency in CD8$^+$ T cells[2] |
|---|---|---|---|---|
| SFV-eE6,7 | 1 × 10$^6$ | 18 days | 1 in 6557 | 1 in 524 |
| SFV-eE6,7 | 2.5 × 10$^6$ | 18 days | 1 in 1785 | 1 in 143 |
| SFV-eE6,7 | 5 × 10$^6$ | 18 days | 1 in 4081 | 1 in 326 |
| SFV-eE6,7 | 1 × 10$^6$ | 8 weeks | 1 in 5381 | 1 in 430 |
| SFV-eE6,7 | 2.5 × 10$^6$ | 8 weeks | 1 in 13,636 | 1 in 1090 |
| SFV-eE6,7 | 5 × 10$^6$ | 8 weeks | 1 in 7692 | 1 in 615 |
| SFV-LacZ | 5 × 10$^6$ | 18 days and 8 weeks | 0 in 4 × 10$^5$ | — |
| PBS | | 18 days and 8 weeks | 0 in 4 × 10$^5$ | — |

Mice were immunized s.c. and boosted twice (s.c. and i.p.) with 1,2.5 or 5 × 10$^6$ SFV-eE6,7 or with 5 × 10$^6$ SFV-LacZ or PBS as controls.
[1]Spleen cells were isolated 18 days or 8 weeks after the last booster immunization and the frequency of precursor CTLs was determined by INF-γ Elispot assay upon overnight in vitro stimulation with 13-2 cells expressing HPV16-E7 49–57 (MHC class I epitope).
[2]Calculated frequency using a CD8 frequency of 8% of the total spleen.

TABLE 2

Protection from growth of TC-1 tumor cells in SFV-eE6,7 immunized mice upon tumor challenge and re-challenge.

| Immunization[1] | Number of tumor-free mice after 1$^{st}$ tumor challenge/total number of mice[2] | Number of tumor-free mice after 2$^{nd}$ tumor challenge/total number of mice[3] |
|---|---|---|
| Exp. 1 Tumor challenge day 0, tumor re-challenge week 25 | | |
| SFV-eE6,7 (1 × 10$^6$) | 4/5 | 2/4 |
| SFV-LacZ (1 × 10$^6$) | 0/5 | — |
| PBS | 0/5 | 0/3[4] |
| Exp. 2 Tumor challenge day 0, tumor re-challenge week 13 | | |
| SFV-eE6,7 (1 × 10$^6$) | 5/5 | 3/5 |
| SFV-eE6,7 (5 × 10$^6$) | 4/5 | 4/4 |
| SFV-LacZ (5 × 10$^6$) | 0/5 | — |
| PBS | 0/5 | 0/3[4] |

[1]Mice were immunized s.c. and boosted twice (s.c. and i.p.) with 1 × 10$^6$ or 5 × 10$^6$ SFV-LacZ particles on SFV-eE6,7 particles or PBS. One week after the last booster immunization, 2 × 10$^4$ TC-1 tumor cells were inoculated s.c. in the neck.
[2]Tumor growth was monitored twice weekly. The number of tumor-free mice per total number of mice per group are shown.
[3]Mice that remained tumor-free were subsequently re-challenged with 2 × 10$^4$ TC1 cells. In the 1$^{st}$ experiment in week 25, in the 2$^{nd}$ experiment in week 13 after the first tumor challenge.
[4]In the re-challenge experiments, three age-matched control mice were included.

REFERENCES

Zur Hausen H. Viruses in human cancer. *Science* 1991; 254: 1167–1173.

Münger K., Scheffner M., Huibregtse J. M., Howley P. M. Interactions of HPV E6 and E7 with tumor suppressor gene products. *Cancer Surv.* 1992; 12: 197–217.

Werness B. A., Levine A. J., Howley P. M. Association of human papillomavirus types 16 and 18 E6 proteins with p53. *Science* 1990; 248: 76–79.

Pei X. F. The human papillomavirus E6/E7 genes induce discordant changes in the expression of cell growth regulatory proteins. *Carcinogenesis* 1996; 17: 1395–1401.

Jones D. L., Münger K. Interactions of human papillomavirus E7 protein with cell cycle regulators. *Seminars Cancer Biol.* 1996; 7: 327–337.

Gulliver G. A., Herber R. L., Liem A., Lambert P. F. Both conserved region 1 (CR1) and CR2 of the human papillomavirus type 16 E7 oncogene are required for induction of epidermal hyperplasia and tumor formation in transgenic mice. *J. Virol.* 1997; 71: 5905–5914.

Porreco R. et al. Gynecological malignancies in immunosuppressed organ homograft recipients. *Obstet. Gynecol.* 1975; 45: 359–364.

Johnson J. C. et al. High frequency of latent and clinical human papillomavirus cervical infections in immunocompromised human immunodeficiency virus-infected women. *Obstet. Gynecol.* 1992; 79: 321–327.

Feltkamp M. C. et al. Vaccination with cytotoxic T lymphocyte epitope containing peptide protects against a tumor induced by human papillomavirus type 16-transformed cells. *Eur. J Immunol.* 1993; 23: 2242–2249.

Feltkamp M. C. et al. Cytotoxic T lymphocytes raised against a subdominant epitope offered as a synthetic peptide eradicate human papillomavirus type 16-induced tumors. *Eur. J. Immunol.* 1995; 25: 2638–2642.

Jochmus I. et al. Specificity of human cytotoxic T lymphocytes induced by a human papillomavirus type 16 E7-derived peptide. *J. Gen. Virol.* 1997; 78: 1689–1695.

De Bruijn M. L. et al. Immunization with Human Papillomavirus Type 16 (HPV16) Oncoprotein-loaded dendritic cells as well as protein in adjuvant induces MHC Class I-restricted protection to HPV16-induced tumor cells. *Cancer Res.* 1998; 58: 724–731.

Strauss J. H., Strauss E. G. The alphaviruses: gene expression, replication, and evolution. *Microbiology Reviews* 1994; 58: 491–562.

Liljeström P., Lusa S., Huylebroeck D., Garoff H. In vitro mutagenesis of a full-length cDNA clone of Semliki Forest virus: the small 6,000-molecular-weight membrane protein modulates virus release. *J. Virol.* 1991; 65: 4107–4113.

Liljeström P., Garoff H. A new generation of animal cell expression vectors based on the Semliki Forest virus replicon. *Biotechnol.* 1991; 9: 1356–1361.

Berglund P. et al. Semliki Forest virus expression system: Production of conditionally infectious recombinant particles. *Biotechnol.* 1993; 11: 916–920.

Sedman S. A. et al. The full-length E6 protein of Human Papillomavirus type 16 has transforming and trans-activating activities and cooperates with E7 to immortalize keratinocytes in culture. *J. Virol.* 1991; 65: 4860–4866.

Greenfield I., Nickerson J., Penman S., Stanley M. Human papillomavirus 16 E7 protein is associated with the nuclear matrix. *Proc. Natl. Acad. Sci. USA* 1991; 88: 11217–11221.

Nindl I. et al. The E7 protein of human papillomavirus (HPV) type 16 expressed by recombinant vaccinia virus can be used for detection of antibodies in sera from cervical cancer patients. *J. Virol. Methods* 1996; 62: 81–85.

Braspenning J. et al. A general purification protocol for E7 proteins from Ahigh- and low-risk@ Human Papillomavirus types expressed in the yeast *Schizosaccharamyces pombe*. *Protein Expression Purif.* 1997; 10: 192–201.

Grossman S. R., Mora R., Laimins L. A. Intracellular localization and DNA-binding properties of human papillomavirus type 18 E6 protein expressed with a baculovirus vector. *J. Virol.* 1989; 63: 366–374.

Daniels P. R., Sanders C. M., Maitland N. Y. Characterization of the interactions of human papillomavirus type 16 E6 with p53 and E6-associated protein in insect and human cells. *J. Gen. Virol.* 1998; 79: 489–499.

Toes R. E. M. et al. Peptide vaccination can lead to enhanced tumor growth through specific T-cell tolerance induction. *Proc. Natl. Acad. Sci. USA* 1996; 93: 7855–7860.

Boursnell M. E. G. et al. Construction and characterization of a recombinant vaccinia expressing Human Papillomavirus proteins for immunotherapy of cervical cancer. *Vaccine* 1996; 14: 1485–1494.

Lin K. Y. et al. Treatment of established tumors with a novel vaccine that enhances major histocompatibility class II presentation of tumor antigen. *Cancer Res.* 1996; 56: 21–26.

Chen L. et al. Induction of cytotoxic T lymphocytes specific for a syngeneic tumor expressing the E6 oncoprotein of human papillomavirus type 16. *J. Immunol.* 1992; 148: 2617–2621.

Borysiewicz L. K. et al. A recombinant vaccinia virus encoding human papillomavirus types 16 and 18, E6 and E7 proteins as immunotherapy for cervical cancer. Lancet 1996; 347: 1523–1527.

Glasgow G. M., McGee M. M., Sheahan B. J., Atkins G. J. Death mechanisms in cultured cells infected by Semliki Forest virus. *J. Gen. Virol.* 1997; 78: 1559–1563.

Berglund P., Fleeton M. N., Smerdou C., Liljeström P. Immunization with recombinant Semliki Forest virus induces protection against influenza challenge in mice. *Vaccine* 1999; 17: 497–507.

Rock K. L. A new foreign policy: MHC class I molecules monitor the outside world. *Immunol. Today* 1996; 17: 131–137.

Bennett S. R. M. Help for cytotoxic-T-cell responses is mediated by CD40 signaling. *Nature* 1998; 393: 478–480.

Lanzavecchia A. Immunology. License to kill. *Nature* 1998; 393: 413–414.

Ridge J. P., Di Rosa F., Matzinger P. A conditioned dendritic cell can be a temporal bridge between a CD4+ T-helper and a T-killer cell. *Nature* 1998; 393: 474–478.

Schoenberger S. P. et al. T-cell help for cytotoxic T lymphocytes is mediated by CD40-CD40L interactions. *Nature* 1998; 393: 480–483.

Zhou X. et al. Generation of cytotoxic and humoral immune responses by nonreplicative recombinant Semliki Forest virus. *Proc. Natl. Acad. Sci. USA* 1995; 92: 3009–3013.

Berglund P. et al. Outcome of immunization of Cynomolgus monkeys with recombinant Semliki Forest virus encoding Human Immunodeficiency virus type I envelope protein and challenge with a high dose of SHIV-4 virus. *AIDS Res. Hum. Retroviruses* 1997; 13: 1487–1495.

Smerdou C., Liljeström P. Two-helper RNA system for production of recombinant Semliki forest virus particles. *J. Virol.* 1999; 73: 1092–1098.

Smits P. H. M., Smits H. L., Jebbink M. F., Ter Schegget J. The short arm of chromosome 11 likely is involved in the regulation of the human papillomavirus type 16 early enhancer-promoter and in the suppression of the transforming activity of the viral DNA. *Virol.* 1990; 176: 158–165.

What is claimed is:

1. An Semliki Forest Virus vector system comprising a nucleic acid molecule of human papilloma virus (HPV) origin, wherein said nucleic acid molecule encodes at least one antigenic polypeptide fragment of an E6 or an E7 protein of HPV.

2. The Semliki Forest Virus vector system of claim 1, wherein said antigenic polypeptide fragment comprises an antigenic polypeptide fragment of protein E6 and an antigenic polypeptide fragment of protein E7.

3. The Semliki Forest Virus vector system of claim 1, further comprising a translational enhancer element.

4. The Semliki Forest Virus vector system of claim 1, further comprising a sequence encoding an auto-protease.

5. The Semliki Forest Virus vector system of claim 4, wherein said auto-protease is of foot-and-mouth-disease virus origin.

6. The Semliki Forest Virus vector system of claim 1, wherein comprising an alphavirus structural protein and an alphavirus non-structural protein encoded by at least two independent nucleic acid molecules.

7. The Semliki Forest Virus vector system of claim 1, wherein said HPV comprises HPV16 or HPV18.

8. The Semliki Forest Virus vector system of claim 1, wherein said nucleic acid molecule further encodes a cytokine or a functional fragment thereof.

9. The Semliki Forest Virus vector system of claim 8, wherein said cytokine comprises Granulocyte-Macrophage Colony-Stimulating-Factor or IL12.

10. A cell comprising the Semliki Forest Virus vector system of claim 1.

11. A medicament comprising the Semliki Forest Virus vector system of claim 1.

12. A medicament comprising the cell of claim 10.

13. A method for treating or preventing cervical cancer, said method comprising administering the Semliki Forest Virus vector system of claim 1 to a female subject.

14. A method for treating or preventing cervical cancer, said method comprising administering the cell of claim 10 to a female subject.

15. A method for treating or preventing cervical cancer, said method comprising administering the medicament of claim 11 to a female subject.

16. The method according to claim 13, further comprising administering a cytokine or a functional fragment thereof to the female subject.

17. The Semliki Forest Virus vector system of claim 2, further comprising a translational enhancer element.

18. The Semliki Forest Virus vector system of claim 2, further comprising a sequence encoding an auto-protease.

19. The Semliki Forest Virus vector system of claim 18, wherein said auto-protease is of foot-and-mouth-disease virus origin.

20. The Semliki Forest Virus vector system of claim 2, wherein said Semliki Forest Virus vector system comprises an alphavirus structural protein and an alphavirus non-structural protein are encoded by at least two independent nucleic acid molecules.

21. The Semliki Forest Virus vector system of claim 2, wherein said HPV comprises HPV16 or HPV18.

22. The Semliki Forest Virus vector system of claim 2, wherein said nucleic acid molecule further encodes a cytokine or a functional fragment thereof.

23. The Semliki Forest Virus vector system of claim 22, wherein said cytokine comprises Granulocyte-Macrophage Colony-Stimulating-Factor or IL 12.

24. A cell comprising the Semliki Forest Virus vector system of claim 2.

25. A composition comprising the cell of claim 24.

26. A composition comprising the Semliki Forest Virus vector system of claim 2.

27. A method of treating or preventing cervical cancer, said method comprising administering the Semliki Forest Virus vector system of claim 2 to a subject in need thereof.

28. The method according to claim 27, further comprising administering a cytokine to the subject.

* * * * *

UNITED STATES PATENT AND TRADEMARK OFFICE
CERTIFICATE OF CORRECTION

PATENT NO. : 7,198,792 B2  
APPLICATION NO. : 10/406818  
DATED : April 3, 2007  
INVENTOR(S) : Djoeke Geesje Regts et al.

Page 1 of 1

It is certified that error appears in the above-identified patent and that said Letters Patent is hereby corrected as shown below:

|  |  |  |
|---|---|---|
|  | COLUMN 18, LINE 15, | change "The (Netherlands)" to --The Netherlands)-- |
|  | COLUMN 18, LINE 22, | change "The (Netherlands)." to --The Netherlands).-- |
|  | COLUMN 18, LINE 36, | change "(E7reverse)." to --(E7 reverse).-- |
|  | COLUMN 20, LINE 20, | change "after the, last booster" to --after the last booster-- |
|  | COLUMN 22, LINE 24, | change "$5\times10^{\,6}$" to --$5\times10^6$-- |
| CLAIM 6, | COLUMN 33, LINE 7, | at the beginning of the line delete "wherein" |
| CLAIM 23, | COLUMN 34, LINE 21, | change "IL 12." to --Il12.-- |

Signed and Sealed this

Fourteenth Day of July, 2009

JOHN DOLL  
*Acting Director of the United States Patent and Trademark Office*